US008871901B2

(12) United States Patent
Samoylova et al.

(10) Patent No.: US 8,871,901 B2
(45) Date of Patent: Oct. 28, 2014

(54) PHAGE CONSTRUCTS, SEQUENCES AND ANTIGENIC COMPOSITIONS FOR IMMUNOCONTRACEPTION OF ANIMALS

(75) Inventors: Tatiana I. Samoylova, Auburn, AL (US); Nancy R. Cox, Auburn, AL (US); Alexandre M. Samoylov, Auburn, AL (US); Anna M. Cochran, Auburn, AL (US); Valery A. Petrenko, Auburn, AL (US)

(73) Assignee: Auburn University, Auburn, AL (US)

( * ) Notice: Subject to any disclaimer, the term of this patent is extended or adjusted under 35 U.S.C. 154(b) by 611 days.

(21) Appl. No.: 13/069,006

(22) Filed: Mar. 22, 2011

(65) Prior Publication Data
US 2011/0311565 A1 Dec. 22, 2011

Related U.S. Application Data

(60) Provisional application No. 61/316,203, filed on Mar. 22, 2010, provisional application No. 61/316,211, filed on Mar. 22, 2010.

(51) Int. Cl.
A61P 15/16 (2006.01)
A61P 15/18 (2006.01)
A61K 38/00 (2006.01)
C07K 7/00 (2006.01)
A61K 39/00 (2006.01)
C07K 7/06 (2006.01)

(52) U.S. Cl.
CPC ......... *A61K 39/0006* (2013.01); *A61K 2039/53* (2013.01); *A61K 2039/60* (2013.01); *C07K 7/06* (2013.01)
USPC ............. 530/328; 530/326; 530/327; 514/9.8

(58) Field of Classification Search
USPC .................................. 530/326–328; 514/9.8
See application file for complete search history.

(56) References Cited

U.S. PATENT DOCUMENTS

| | | | |
|---|---|---|---|
| 6,383,496 B1 | 5/2002 | Curtiss, III et al. | |
| 6,620,923 B1 * | 9/2003 | Specht et al. | 536/23.1 |
| 6,923,958 B2 | 8/2005 | Xiang et al. | |
| 7,094,868 B2 | 8/2006 | Samoylova et al. | |
| 7,745,391 B2 * | 6/2010 | Mintz et al. | 514/19.3 |
| 2004/0123343 A1 * | 6/2004 | La Rosa et al. | 800/278 |
| 2007/0039067 A1 * | 2/2007 | Feldmann et al. | 800/278 |
| 2007/0079401 A1 * | 4/2007 | Lough et al. | 800/287 |
| 2009/0280137 A1 * | 11/2009 | Samoylova et al. | 424/184.1 |
| 2011/0044989 A1 | 2/2011 | Samoylova et al. | |
| 2011/0296543 A1 * | 12/2011 | Chang et al. | 800/13 |

FOREIGN PATENT DOCUMENTS

| | | | | |
|---|---|---|---|---|
| WO | WO 2007/132461 | * | 11/2007 | G06F 19/00 |
| WO | WO 2008/151636 | * | 12/2008 | C12N 15/52 |
| WO | WO 2009/091518 | * | 7/2009 | A01H 5/00 |
| WO | WO 2009/099580 | * | 8/2009 | A01H 5/00 |
| WO | 2009126648 | | 10/2009 | |

OTHER PUBLICATIONS

Betts et al., 2003, Chapter 14 Amino Acid Properties and Consequences of Substitutions, Bioinformatics for Geneticists, 28 pages.*
Abdennebi et al., "Generating FSH antogonists and agonists through immunization against FSH receptor N-terminal decapeptides", Journal of Molecular Endocrinology, 1999, 22:151-159.
Brigati et al., "Thermostability of landscape phage probes", Anal Bioanal Chem, 2005, 382:1346-1350.
Chamley et al., "Antisperm antibodies and conception", Semin Immunopathol, 2007, 29:169-184.
Conner et al., "Cracking the egg: increased complexity in the zona pellucida", Human Reproduction, 2005, 20 (5):1148-1152.
Cowled et al., "Vaccination of feral pigs (*Sus scrofa*) using iophenoxic acid as a simulated vaccine", Australian Veterinary Journal, January, Feb. 2008, 86(1, 2):50-55.
Daudel et al., "Use of attenuated bacteria as delivery vectors for DNA vaccines", Expert Review of Vaccines, Feb. 2007, 14:97-110.
Ditchkoff et al., "Ecology and management of feral hogs", Human-Wildlife Conflicts, Fall 2007, 1(2):149-151.
Dunbar et al., "Characterization of Porcine Zona Pellucida Antigens", Biology of Reproduction, 1980, 22:941-954.
Eriksson et al., "Tumor specific phage particles promote tumor regression in a mouse melanoma model", Cancer Immunol Immunother, 2007, 56:677-687.
Eriksson et al., "Tumor-Specific Bacteriophages Induce Tumor Destruction through Activation of Tumor-Associated Macrophages", Journal of Immunology, 2009, 182:3105-3111.
Fehr et al., "T cell-independent type I antibody response against B cell epitopes expressed repetitively on recombinant particles", Proc. Natl. Acad. Sci. USA, Aug. 1998, 95:9477-9481.
Frenkel et al., "Reduction of beta-amyloid plaques in brain of transgenic mouse model of Alzheimer's disease by EFRH-phage immunization", Vaccine, 2003, 21:1060-1065.
Garmory et al., "The Use of Live Attenuated Bacteria as a Delivery System for Heterologous Antigens", Journal of Drug Targeting, 2003, 11(8-10):471-479.
Gaubin et al., "Processing of Filamentous Bacteriophage Virions in Antigen-Presenting Cells Targets Both HLA Class I and Class II Peptide Loading Compartments", DNA and Cell Biology, 2003, 22(1):11-18.
Gentschev et al., "Recombinant attenuated bacteria for the delivery of subunit vaccines", Vaccine, 2001, 19:2621-2628.
Hammond et al., "Porcine adenovirus as a delivery system for swine vaccines and immunotherapeutics", The Veterinary Journal, 2005, 169:17-27.
Hutton et al., "Disease Risks Associated with Increasing Feral Swine Numbers and Distribution in the United Stated", Midwest Association of Fish and Wildlife Agencies Wildlife and Fish Health Committee, Jul. 11, 2006, 15 pages.

(Continued)

*Primary Examiner* — Amber D Steele

(74) *Attorney, Agent, or Firm* — Andrus Intellectual Property Law, LLP

(57) ABSTRACT

Disclosed are methods, compositions, zona pellucida binding peptides and polypeptides, and expression vectors for use in species-specific immunocontraception of animals, which include landscape bacteriophage. The disclosed compositions may include immunogenic compositions or vaccines.

12 Claims, 9 Drawing Sheets

(56) References Cited

OTHER PUBLICATIONS

Killian et al., "Immunocontraception of Florida Feral Swine with a Single-dose GnRH Vaccine", American Journal of Reproductive Immunology, 2006, 55:378-384.

Krag et al., "Selection of Tumor-binding Ligands in Cancer Patients with Phage Display Libraries", Cancer Research, 2006, 66:7724-7733.

Miller et al., "Immunocontraception of White-Tailed Deer with GnRH Vaccine", American Journal of Reproductive Immunology, 2000, 44:266-274.

Petrenko et al., "A library of organic landscapes on filamentous phage", Protein Engineering, 1996, 9(9):797-801.

Samoylova et al., "Identification of Cell targeting Ligands Using Random Peptide-Presenting Phage Libraries", Springer Lab Manual- RC Bird, BF Smith (Eds.), Genetic Library Construction and Screening, 2002, 209-231.

Shata et al., "Receipt advances with recombinant bacterial vaccine vectors", Molecular Medicine Today, Feb. 2000, 6:66-71.

Suri, "Contraceptive vaccines targeting sperm", Expert Opin. Biol. Ther., 2005, 5(3):381-392.

Suri, "Sperm-based contraceptive vaccines: current status, merits and development", Expert Reviews in Molecular Medicine, Sep. 12, 2005, 7(18):1-16.

Yip et al., "Comparison of phage pIII, pVIII and GST as carrier proteins for peptide immunisation in Balb/c mice", Immunology Letters, 2001, 79:197-202.

Invitation to Pay Additional Fees and, Where Applicable, Protest Fee dated Jun. 24, 2011 for PCT/US2011/029408, 6 pages.

Examination Report for EP11711422.3 dated Sep. 9, 2013, 4 pages.

International Search Report for PCT/US2011/029408 dated Jun. 6, 2011, 6 pages.

Written Opinion for PCT/US2011/029408 dated Jun. 6, 2011, 9 pages.

Bachmann et al., "Neutralizing antiviral b cell responses", Annu. Rev. Immunol., 1997, 15:235-270.

Ballesteros et al., "Evaluation of baits for oral vaccination of european wild boar piglets", Research in Veterinary Science, 2009, 86:388-393.

Clare et al., "Live recombinant bacteria vaccines", Novel Vaccination Strategies, 2004, 319-341.

De Berardinis et al., "Use of fusion proteins and procaryotic display system for delivery of HIV-1 antigens: development of novel vaccines for HIV-1 infection", Current HIV Research, 2003, 1:441-446.

De Berardinis et al., "New recombinant vaccines based on the use of prokaryotic antigen-display systems", Future Drugs, 2004, 673-679.

Hashemi et al., "Evaluation of humoral and cellular immune responses against HSV-1 using genetic immunization by filamentous phage particles: a comparative approach to conventional DNA vaccine", Journal of Virological Methods, 2010, 163:440-444.

Houimel et al., "Peptide mimotopes of rabies virus glycoprotein with immunogenic activity", Vaccine, 2009, 27:4648-4655.

Kaden et al., "Oral immunisation of wild boar against classical swine fever: evaluation of the first field study in Germany", Veterinary Microbiology, 2000, 73:239-252.

Manoutcharian et al., "Phage displayed biomolecules as preventive and therapeutic agents", Current Pharmaceutical Biotechnology, 2001, 2:217-223.

Minenkova et al., "Design of specific immunogens using filamentous phage as the carrier", Gene, 1993, 85-88.

Rao et al., "Induction of infertility in adult male bonnet monkeys by immunization with phage-expressed peptides of the extracellular domain of FSH receptor", Reproductive BioMedicine, 2004, 8(4):385-391.

Samoylova et al., "ZP-binding peptides indentified via phage display stimulate production of sperm antibodies in dogs", Animal Reproduction Science, 2010, 120:151-157.

Ulivieri et al., "Antigenic properties of HCMV peptides displayed by filamentous bacteriophages vs. synthetic peptides", Immunology Letters, 2008, 119:62-70.

Wan et al., "Cross-presentation of phage particle antigen in MHC class II and endoplasmic reticulum marker-positive compartments", Eur. J. Immunol., 2005, 35:2041-2050.

Wang et al., "Protective immune responses against systemic candidiasis mediated by phage-displayed specific epitope of Candida albicans heat shock protein 90 in C57BL/6J mice", Vaccine, 2006, 24:6065-6073.

Yang et al., "Production of hybrid phage displaying secreted aspartyl proteinase epitope of Candida albicans and its application for the diagnosis of disseminated candidiasis", Mycoses, May 2007, 50(3):165-171.

Extended European Search Report for EP13197771 dated Jan. 31, 2014.

\* cited by examiner

LEVEL I

PHAGE DISPLAY
PEPTIDE LIBRARY

↓ REACT

OOCYTES
CAT

↓

OOCYTES
DOG

↓

OOCYTES
COW

↓

OOCYTES
PIG

↓

IDENTIFY PIG ZP-
BINDING PEPTIDE(S)

LEVEL II

INSERT PEPTIDE-CODING
SEQUENCE INTO SP-SP
VIRUS / BACTERIA

LEVEL III

DELIVER VACCINE TO PIGS
IN PIG-PREFERRED BAIT

IMMUNE RESPONSES TO THE
VACCINE BLOCK FERTILIZATION

FIG. 4

PHAGE DISPLAY
PEPTIDE LIBRARY

CAT   DOG   COW   PIG   RECOVER
                        BOUND
                        PHAGE

FIG. 5

```
                SEQUENCES
SEQ ID NO:1    -DADDQTHRRFSM
SEQ ID NO:2    -DANRLPHPANIN
SEQ ID NO:3    -DLNGHKTLPVSK
SEQ ID NO:4    -NIGLPHDLHKRL
SEQ ID NO:5    -GLHNNLHATTPE
SEQ ID NO:6    -QSAAWYPWSADH
SEQ ID NO:7    -YTVSMPNVKDAA
SEQ ID NO:8    -YMPNPFTASKWK
SEQ ID NO:9    -GQIMPLPTNLLV
SEQ ID NO:10   -STTLPMGSNAHL
SEQ ID NO:11   -TYLKADSLFSRV

MOTIFS
SEQ ID NO:12   -TTLXTXSXXHXX
SEQ ID NO:13   -DXNXLPHXXXXX
SEQ ID NO:14   -XGLXXXLHXTXP
SEQ ID NO:15   -XXMPN{P,V}XXAX
SEQ ID NO:16   -X{G,S}XXTLPXSX
SEQ ID NO:17   -QXAXXXPWXXXX
```

FIG. 7

```
                SEQUENCES
SEQ ID NO:2    -DANRLPHPANIN
SEQ ID NO:18   -TLGWTANEAPRR
SEQ ID NO:19   -LLADTTHHRPWT
SEQ ID NO:20   -SQSPAMYSQTRP
SEQ ID NO:21   -AVTQHLKFKGFN
SEQ ID NO:22   -ANFNMTHHQGHK

MOTIFS
SEQ ID NO:23   -XXTTHHXXXXXX
SEQ ID NO:24   -XXNXXLXXPAXX
SEQ ID NO:25   -XXAXXXXXRPXX
SEQ ID NO:26   -XXSSXXSASXXX
```

FIG. 8

1. YLPVGGLRRIGG (SEQ ID NO:57) (CONTROL FROM LITERATURE)
2. YMPNPFTASKWK (SEQ ID NO:8) – EX. 1
3. AVTQHLKFKGFN (SEG ID NO:21) – EX. 2
4. LLADTTHHRPWT (SEQ ID NO:19) – EX. 2
5. TLGWTANEAPRR (SEQ ID NO:18) – EX. 2
6. DANRLPHPANIN (SEQ ID NO:2) – EX. 1, EX. 2
7. SQSPAMYSQTRP (SEQ ID NO:20) – EX. 2

SEMEN QUALITY / TESTOSTERONE LEVEL
TESTICLE WIDTH

| PHAGE CLONE | SPERM COUNT / EJACULATE* | SPERM MOTILITY | TESTOSTERONE RANGE^, ng/ml | TESTICLE WIDTH, mm BEFORE tr/16 MONTH LATER |
|---|---|---|---|---|
| 3.3 | 2.9x10^8 | 85% | 0.3–4.4 | 21.5 / 20.3 |
| 3.1 | NO LIBIDO | NO LIBIDO | 0.7–8.0 | 18.5 / 18.3 |
| 3.7 | 2.5x10^8 | 69% | 1.7–6.8 | 21.3 / 19.6 |
| 2.26 | 6.8x10^4 | 60% | 1.0–8.3 | 19.0 / 19.0 |

*NORMAL DOG SPERM COUNT: ~3x10^8 / EJACULATE;
^BLOOD COLLECTED ~SAME TIME OF THE DAY

FIG. 11

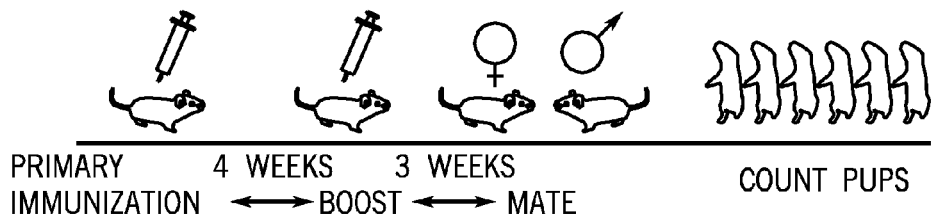

FERTILITY TRIALS IN MICE

PRIMARY IMMUNIZATION ←→ 4 WEEKS BOOST ←→ 3 WEEKS MATE    COUNT PUPS

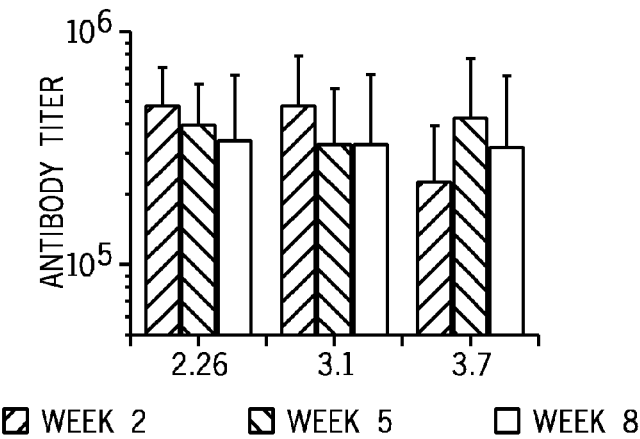

FIG. 12

PHAGE CONSTRUCTS, SEQUENCES AND ANTIGENIC COMPOSITIONS FOR IMMUNOCONTRACEPTION OF ANIMALS

STATEMENT REGARDING FEDERALLY SPONSORED RESEARCH OR DEVELOPMENT

This invention was made with government support under ALA051-08004 and 657AES awarded by the Alabama Agricultural Experient Station. The government has certain rights in the invention.

CROSS-REFERENCE TO RELATED APPLICATIONS

The present application claims the benefit of priority under 35 U.S.C. §119(e) to U.S. provisional application No. 61/316,203, filed on Mar. 22, 2010; and U.S. provisional application No. 61/316,211, filed on Mar. 22, 2010; the contents of which are incorporated herein by reference in their entireties.

BACKGROUND

The present subject matter relates to the field of recombinant bacteriophage constructs and related heterologous peptide sequences for targeted contraception in animals. In particular, the present subject matter relates to peptides and polypeptides that bind to the zona pellucida (ZP) of oocytes, methods for selecting such peptides and polypeptides, vectors or constructs that express the selected peptides and polypeptides, and compositions that comprise such peptides, polypeptides, vectors or constructs (e.g., compositions for inducing an immune response against sperm).

Overpopulation of animals of multiple species including domestic, feral, and wild animals results in various economic, health, and security problems. For example, dog overpopulation remains a serious welfare concern and is a worldwide problem. In the United States, several million domestic dogs enter animal shelters annually and approximately one half are euthanized. Feral free-roaming dogs throughout the world affect the environment generating tons of waste products, consuming small wildlife, and, most of all, harboring dozens of viral, bacterial and parasitic diseases communicable to humans, agricultural animals, and pets.

With respect to feral dogs, "capture and kill" has been the primary strategy used to control populations. However, this strategy has not reduced the magnitude of this serious problem in 100 years because it illogically addresses the result rather than the cause of the problem. The obvious solution is preventing the birth of unwanted animals. Surgical gonadectomy is considered the gold standard and low cost spay/neuter clinics have made limited progress in reducing unwanted dog populations in some locals, but it is not equal to this overwhelming task. While feral dogs are less of a concern in the United States due to active spay and neuter programs, animal shelters and animal control programs are lacking in many developing countries and humane methods of population control are urgently needed. Clearly, an effective, technically uncomplicated and inexpensive method applied on a mass scale is needed.

Feral swine also present a threat to agricultural crops, soils, vineyards, tree plantings, turf, rare plant communities, wildlife habitat, archaeological sites, and vehicles. (See Ditchkoff S S, West B C. Ecology and management of feral hogs. Human-Wildlife Conflicts 2007; 1(2):149-151). Feral swine compete with livestock and native wildlife for food, and prey on domestic animals and wildlife. Feral swine carry at least thirty important viral and bacterial diseases and thirty-seven parasites that affect humans, pets, livestock, and wildlife (e.g., brucellosis, salmonellosis, diseases due to pathogenic E. coli strains, rabies, tuberculosis, and tularemia). Feral swine also could potentially spread additional human and animal diseases not currently found in the United States. (See Hutton T, DeLiberto T, Owen S, Morrison B. Disease risks associated with increasing feral swine numbers and distribution in the United States. Midwest Association of Fish and Wildlife Agencies 2006). Additional examples of species, the overpopulation of which imposes various kinds of economic and health risks, include coyotes, deer, and raccoons.

Control programs for unwanted animals such as poisoning, trapping, shooting, etc., are ineffective, expensive and generally unacceptable to the public. The most efficient solution worldwide is to prevent the birth of unwanted animals. The development of nonsurgical methods of sterilization would provide practical alternatives to surgical neutering. This could be achieved using effective and economically sound contraceptive preparations. However, currently available contraceptives for animals are not selective and affect multiple species and, therefore, cannot be permitted for use in uncontrolled environments such as natural habitats of feral or wild animals. (See Miller L A, Johns B E, Killian G J. Immunocontraception of white-tailed deer with GnRH vaccine. Am J Reprod Immunol 2000; 44(5):266-274; and Killian G, Miller L, Rhyan J, Doten H. Immunocontraception of Florida feral swine with a single-dose GnRH vaccine. American Journal of Reproductive Immunology 2006; 55:378-384). Thus, there is an urgent need for immunocontraceptive, vaccines that can affect the target species only and be delivered via economically sound administration.

SUMMARY

Disclosed are methods, compositions, zona pellucida (ZP)-binding peptides, nucleic acid sequences encoding the ZP-binding peptides, and bacteriophage vectors or constructs for expressing the ZP-binding peptides for use in immunocontraception of animals. The disclosed compositions may include immunogenic or vaccine compositions that comprise ZP-binding peptides, nucleic acid sequences encoding the ZP-binding peptides, or bacteriophage vectors or constructs that express the ZP-binding peptides.

The peptides disclosed herein bind to ZP of animal oocytes. The peptides disclosed herein include, but are not limited to pig oocyte ZP-binding peptides (DPGLSLGDD (SEQ ID NO:41); AYNLGEGDT (SEQ ID NO:42); GQQGLNGDS (SEQ ID NO:43); DVGGGTGTE (SEQ ID NO:44); GPNSSDADS (SEQ ID NO:45); and GEGGYGSHD (SEQ ID NO:46)); dog oocyte ZP-binding peptides (DDLNSFVND (SEQ ID NO:47); ADLAAFYDD (SEQ ID NO:48); EPGGMVGSD (SEQ ID NO:49); DGVYLVGDD (SEQ ID NO:50); DWSGQDVEN (SEQ ID NO:51); and GMVGSGYDS (SEQ ID NO:52)); and cat oocyte ZP-binding peptides (AGSSYTQDS (SEQ ID NO:53); EVNGGSADS (SEQ ID NO:54); EAYPGLDWD (SEQ ID NO:55); and VKSEDPSLN (SEQ ID NO:56)).

The disclosed peptides and polypeptides may be expressed via vectors or constructs that include viral, bacterial, or other vectors or constructs. In some embodiments, the peptide or polypeptides are expressed via a recombinant filamentous bacteriophage (i.e. Ff class phage) where a nucleic acid sequence encoding the peptide or polypeptide is inserted into one or more genes of the bacteriophage (e.g., gene 8). As such, also contemplated are bacteriophage comprising the disclosed peptides and polypeptides, or "landscape phage" as described herein. Preferably, the bacteriophage has only one copy of gene 8 rather than two copies of gene 8 and the nucleic acid sequence encoding the peptide or polypeptide is inserted into the single copy of gene 8. The bacteriophage comprising the disclosed peptides or polypeptides may be inactivated prior to subsequent use in an immunogenic or vaccine composition.

The compositions disclosed herein may comprise any one or more of: (1) the presently disclosed peptides and polypeptides; (2) nucleic acid sequences encoding the disclosed peptides and polypeptides; (3) landscape phage comprising the disclosed peptides and polypeptides; and (4) other viral or bacterial vectors that express the disclosed peptides and polypeptides. The disclosed compositions may be immunogenic or vaccinogenic and may be administered to animals for immunocontraception via induction of an anti-sperm immune response (e.g., species-specific immunocontraception via induction of a species-specific anti-sperm immune response).

The disclosed methods include methods for identifying a peptide or polypeptide that binds specifically to the zona pellucida of oocytes from a target species of animal. The methods may include: (a) isolating oocytes from one or more target species (e.g., porcine oocytes, canine oocytes, feline oocytes, or bovine oocytes); (b) contacting the oocytes with a phage library; (c) selecting phage that bind specifically to the oocytes of a target species of animal (e.g. phage that bind specifically to the oocytes of target species of animal as compared to oocytes from other animals), thereby identifying peptides that bind to the ZP of the oocytes of the target animal species. The methods optionally may include: (a) contacting oocytes of one or more species of animal with a phage library; (b) separating phage that do not bind to the oocytes of one or more non-target species of animal from the phage library; and (c) contacting the separated phage with oocytes of a target species of animal; and (d) separating phage that bind to the oocytes of the target species of animal, thereby identifying peptides that selectively bind to the ZP of the oocytes of the target animal species. Alternatively, the methods may include: (a) contacting oocytes of one or more species of animal with a phage library; (b) separating phage that bind to the oocytes of the target species of animal from the phage library; and (c) contacting the separated phage with oocytes of one or more non-target species of animal; and (d) separating phage that do not bind to the oocytes of the one or more non-target species of animal, thereby identifying peptides that selectively bind to the ZP of the oocytes of the target animal species. In the disclosed methods, the phage library may be contacted with a relatively small number of oocytes (e.g., less than about 1000 oocytes).

Also disclosed are polynucleotides encoding peptides that bind to ZP of animal oocytes. The polynucleotide may be operably linked to a promoter sequence as a recombinant polynucleotide. The recombinant polynucleotide may be present in a vector which is utilized to transform an isolated cell. Preferably, the vector is capable of expressing the encoded peptide or polypeptide. The encoded peptide may be produced by a method that includes: a) culturing the transformed cell under conditions suitable for expression of the peptide; and b) recovering the polypeptide so expressed. Alternatively, the peptide may be prepared by a synthetic method.

The peptides disclosed herein may be utilized as antigens. In some embodiments, the identified peptides may be modified to enhance antigenicity. For example, the peptides may be conjugated to one or more carrier proteins. In some embodiments, the peptides are expressed on the surface of a phage such as a landscape phage as described herein.

The disclosed compositions may include immunogenic compositions or vaccine compositions. In some embodiments, the compositions include (a) one or more peptides comprising an amino acid sequence selected from a group consisting of SEQ ID NOS:1-56; and (b) a suitable excipient, carrier, or diluent. For example, the compositions may include two or more polypeptides, where each of the two or more polypeptides comprise an amino acid sequence selected from a group consisting of SEQ ID NOS:1-56.

Optionally, the immunogenic compositions or vaccine compositions may further include an adjuvant as disclosed herein. Optionally, the immunogenic compositions or vaccine compositions further may include an immunostimulatory agent (e.g., an immunostimulatory oligodeoxynucleotide such as CpG).

Also disclosed are vectors that express the disclosed peptides or polypeptides. Suitable vectors include, but are not limited to, viral vectors and bacterial vectors. The vector may be species-specific (e.g., a viral vector that specifically infects a target species and does not infect a non-target species). The vectors may be formulated as an immunogenic composition or a vaccine composition. In some embodiments, the immunogenic compositions or vaccine compositions comprise one or more vectors (e.g., species-specific vectors) that express one or more peptides or polypeptides (e.g. species-specific ZP-binding peptides or polypeptides).

Also disclosed are methods for using the presently disclosed immunogenic or vaccine compositions that comprise ZP-binding peptides, nucleic acid sequences encoding the ZP-binding peptides, or vectors that express the ZP-binding peptides polypeptides. The disclosed methods may include administering the disclosed immunogenic or vaccine compositions to an animal in order to induce an immune response (e.g., an anti-sperm antibody response, a T-cell response, or both). The disclosed methods may include methods for producing antibodies that bind to sperm (e.g., antibodies against sperm of a target species of animal). As such, the compositions may include an effective amount of a peptide or polypeptide (e.g., a ZP-binding peptide) for inducing an immune response against sperm. Alternatively, the compositions may include a vector that expresses an effective amount of a peptide or polypeptide (e.g., a ZP-binding peptide) for inducing an immune response against sperm (e.g., a bacteriophage or other vector). In the methods, the compositions may be administered to an animal of either sex (i.e., male or female). The methods further may include isolating the induced antibodies from a sample obtained from the animal (e.g., from blood or a blood product such as serum or plasma).

The disclosed methods also may include methods for immunizing an animal against conception (i.e., immunocontraceptive methods). The methods may include administering the disclosed immunogenic composition or vaccine compositions to a target species of animal such as a female animal, thereby immunizing the animal against conception. In some embodiments, the animal is immunized for a temporary period of time (e.g., for a period of weeks or months).

BRIEF DESCRIPTION OF THE FIGURES

, FIG. 1. schematically illustrates a landscape phage displaying a foreign peptide via insertion into the pVIII protein.

FIG. 4. illustrates a strategy for species-specific overpopulation control for domestic, feral, or wild animals having three major levels of species-specificity (exemplified for swine in this figure).

FIG. 5. illustrates selection of species-specific ZP-binding peptides using a phage display library. For the peptides to be species-specific, prior to reaction with oocytes of the target species, a phage display library is reacted with oocytes of non-target species that have close homology with respect to ZP proteins.

FIG. 7. provides a list of porcine ZP-binding peptide sequences and motifs identified in Experiment 1 by selection from a PhD-12 phage display library on intact porcine oocytes surrounded by ZP as described in Example 1.

FIG. 8. provides a list of porcine-specific ZP-binding peptide sequences and motifs identified in Experiment 2 by selection from a PhD-12 phage display library on intact porcine oocytes surrounded by ZP subsequent to subtractive selection on non-porcine oocytes (i.e., feline oocytes, canine oocytes, and bovine oocytes).

FIG. 11. illustrates semen quality, testosterone level, and testicle width of dogs immunized with whole landscape phage particles carrying the following peptides: a) phage clone 3.7—EPGGMVGSD (SEQ ID NO:49); b) phage clone 2.26—EVNGGSADS (SEQ ID NO:54); and c) phage clone 3.1—DDLNSFVND (SEQ ID NO:47).

FIG. 12. illustrates fertility trials in outbred mice. Top: Fertility trials design. Bottom: Anti-peptide antibody responses in mice immunized with whole landscape phage particles carrying the following peptides: a) phage clone 3.7—EPGGMVGSD (SEQ ID NO:49); b) phage clone 2.26—EVNGGSADS (SEQ ID NO:54); and c) phage clone 3.1—DDLNSFVND (SEQ ID NO:47). Immunized mice were paired 2 females:1 male. Total number of mice per group: 8 females, 4 males.

DETAILED DESCRIPTION

Figure 1:
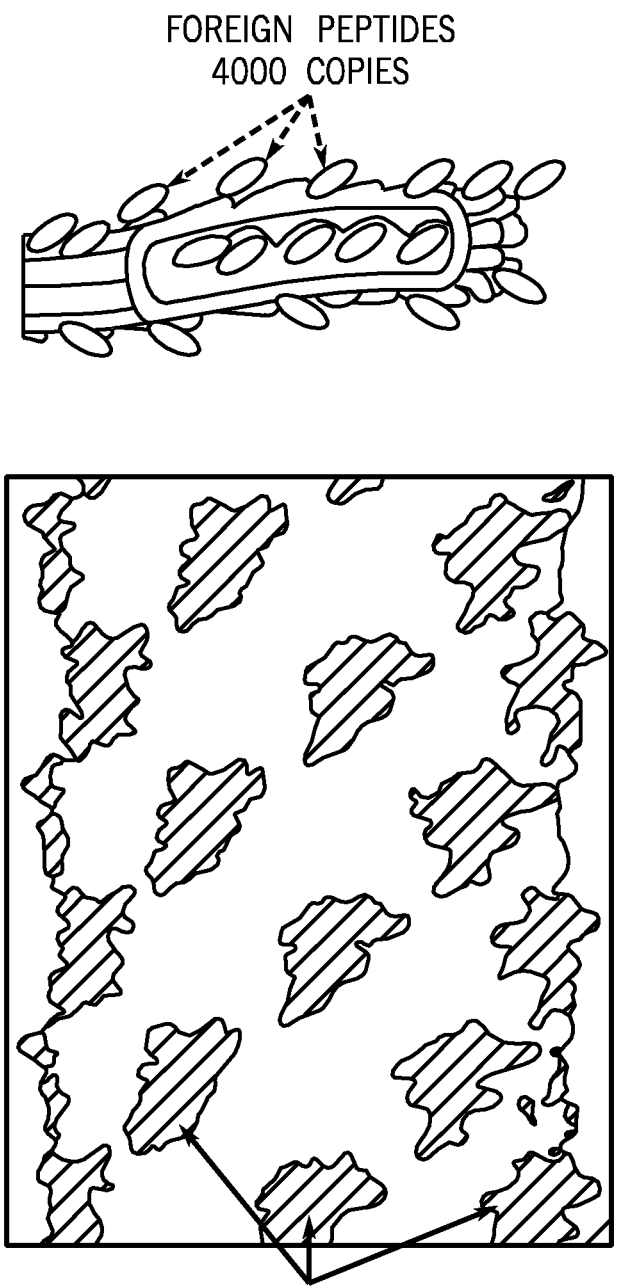
Figure 2:
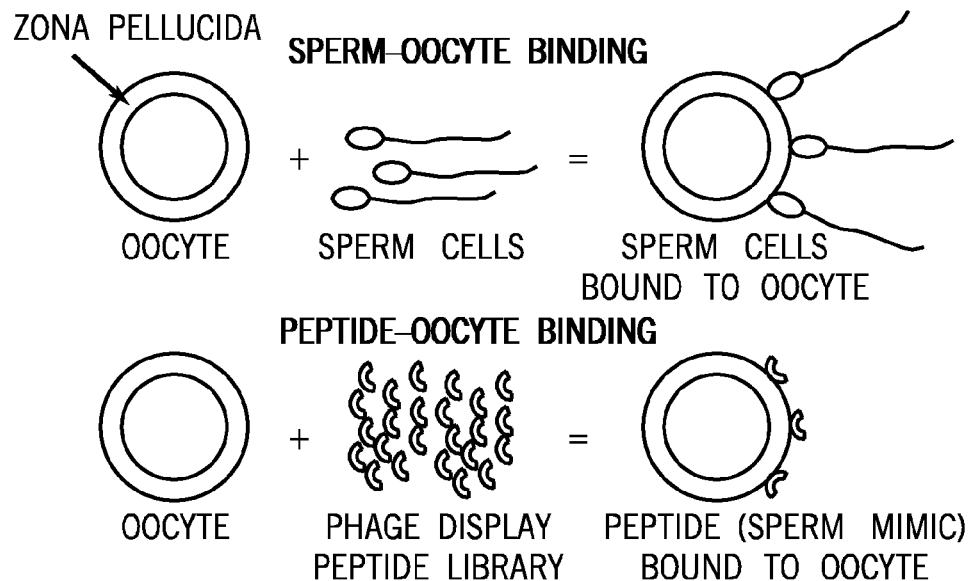
FIG. 2. illustrates a method whereby phage display peptide libraries are used to identify peptides mimicking sperm surface peptides or proteins that bind to zona pellucida at fertilization.

The disclosed subject matter is further described below.

Unless otherwise specified or indicated by context, the terms "a", "an", and "the" mean "one or more." For example, "a peptide" should be interpreted to mean "one or more peptides" unless otherwise specified or indicated by context.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus≤10% of the particular term and "substantially" and "significantly" will mean plus or minus>10% of the particular term.

As used herein, the terms "include" and "including" have the same meaning as the terms "comprise" and "comprising."

The terms "subject" and "patient" may be used interchangeably herein. A patient or subject may refer to a non-human patient or subject at risk for conception. Non-human patients (i.e., animals) may include mammals.

The term "target species" means a species of animal to which the presently disclosed methods, compositions, zona pellucida (ZP)-binding peptides, and vectors for expressing the peptides for use in immunocontraception are specifically targeted relative to a non-target species. Suitable "target species" may include, but are not limited to swine, canine, felines, and bovines.

The term "swine" as used herein is meant to include domesticated, wild, and feral swine (e.g., *Sus scrofa*) and may be used interchangeably with the term "pig" or "porcine." The term "canine" as used herein is meant to include domesticated, wild, and feral canines and may be used interchangeably with the term "dog." The term "feline" as used herein is meant to include domesticated, wild, and feral felines and may be used interchangeably with the term "cat."

The term "sample" is used in its broadest sense. A sample may comprise a bodily fluid (e.g., blood or a blood product such as serum or plasma obtained from a subject or patient).

The disclosed methods may include contacting isolated oocytes with a phage library. As utilized herein, the term "contacting" may include placing the isolated oocytes and the phage library in a reaction vessel and reacting or incubating the isolated oocytes and phage library under conditions that promote interaction between the isolated oocytes and the phage library. The disclosed methods may include separating phage that bind to the oocytes (or that do not bind to the oocytes) from the phage library. As utilized herein, the term "separating" may be utilized interchangeably with the term "isolating" or "removing."

One aspect of the present disclosure relates to methods for isolating peptides and polypeptides that bind to the ZP of oocytes via phage display. Methods for performing phage display are known in the art. (See, e.g., U.S. Pat. No. 7,094, 868, which discloses isolating peptides by phage display, the content of which is incorporated herein by reference in its entirety). Related methods for phage display and isolation of ZP-binding peptides are disclosed in U.S. patent application Ser. No. 12/266,944, filed on Nov. 7, 2008, and published as U.S. Published Application No. 2009-0280137, on Nov. 12, 2009; and U.S. patent application Ser. No. 12/419,883, filed on Apr. 7, 2009, and published as U.S. Published Application No. 2011-0044989, on Feb. 24, 2011, the contents of which are incorporated herein by reference in their entireties.

In particular, the methods disclosed herein may be utilized to isolate peptides and polypeptides that bind selectively to ZP of oocytes of a target species of animal relative to ZP of oocytes of a non-target species of animal via phage display. The methods may include: (a) isolating oocytes from one or more species of animal (e.g., porcine oocytes, feline oocytes, canine oocytes, or bovine oocytes); (b) contacting the oocytes with a phage library; (c) selecting phage that bind to the oocytes (e.g., phage that bind selectively to oocytes of one species of animal), thereby identifying peptides that bind to the ZP of the oocytes. Surprisingly, in the disclosed methods, the phage library may be contacted with a relatively small number of oocytes (e.g., less than about 1000 oocytes). It is generally understood in the field of phage display technology that a significant number of cells (typically millions) are needed for successful selection of cell-binding peptides on intact cells. This significant number of cells is easily achievable for the vast majority of cell types via propagation in cell culture media. However, oocytes cannot be obtained through cell culturing and oocytes with surrounding ZP should be isolated directly from ovaries removed from animals. Generally, only a small number of oocytes can be isolated from a single pair of mammalian ovaries (i.e., as a few as 2-3 and on average, several dozen), depending on the animal species and its age and condition). As such, it would be expected that many animals would be required in order to obtain a sufficient number (millions) of oocytes for phage display selection protocols commonly in use. In addition to the huge numbers of animals needed for isolating a sufficient number of oocytes, the oocyte isolation procedure is very time consuming and generally takes several hours for an experience technician to isolate even a relatively small number of oocytes. Thus, it would take thousands of animals and years of work to isolate the number of oocytes required by currently accepted protocols. For these reasons, millions of oocytes cannot be readily available for the use in phage display selection protocols that are generally utilized in the field. Therefore, herein, a phage display selection procedure that requires no more than 1000 oocytes surrounded by ZP was developed.

The peptides and polypeptides contemplated herein bind specifically to ZP. Furthermore, the peptides and polypeptides contemplated herein may be utilized in immunogenic compositions or vaccines for eliciting antibodies that bind specifically to sperm. In this regard, the terms "binds specifically" and "bind specifically" refer to that interaction between the peptide (or polypeptide) and the ZP; or to that interaction between sperm and an antibody (or other binding molecule). The interaction is dependent upon the presence of a particular structure of the protein, e.g., the antigenic determinant or epitope present on the polypeptide or peptide, recognized by the antibody or binding molecule. For example, if an antibody is specific for epitope "A," the presence of a polypeptide comprising the epitope A, or the presence of free unlabeled A, in a reaction containing free labeled A and the antibody will reduce the amount of labeled A that binds to the antibody.

The peptides and polypeptides disclosed herein may be described via their "amino acid sequence". As used herein, the term "amino acid sequence" refers to amino acid residues joined by amide linkages. The term "amino acid residue," includes but is not limited to amino acid residues contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues. The term "amino acid residue" also may include amino acid residues contained in the group consisting of homocysteine, 2-Aminoadipic acid, N-Ethylasparagine, 3-Aminoadipic acid, Hydroxylysine, β-alanine, β-Amino-propionic acid, allo-Hydroxylysine acid, 2-Aminobutyric acid, 3-Hydroxyproline, 4-Aminobutyric acid, 4-Hydroxyproline, piperidinic acid, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine.

The presently disclosed peptides or polypeptides may be synthetic. As used herein, "synthetic peptide" refers to a peptide which has an amino acid sequence which is not a native sequence or is not in its native context and which confers on phage displaying it the ability to bind or preferentially bind to a particular cell population. By "not in its native context" is intended that the peptide is substantially or essentially free of amino acid sequences that naturally flank the amino acid sequence of the peptide in the native protein which comprises the amino acid sequence of the peptide. For example, a synthetic peptide which is not in its native context may be flanked at either or both ends by no more than 50, 40, 30, 20, 10, 9, 8, 7, 6, 5, 4, 3, 2, or 1 amino acid(s) found in the native protein.

The terms "peptide" and "polypeptide" (and/or "protein") may be used interchangeably herein. However, generally a peptide is defined as a short polymer of amino acids, of a length typically of 20 or less amino acids, and more typically of a length of 12 or less amino acids (Garrett & Grisham, Biochemistry, $2^{nd}$ edition, 1999, Brooks/Cole, 110). In some embodiments, a peptide as contemplated herein may include no more than about 2, 3, 4, 5, 6, 7, 8, 9, 10, 11, 12, 13, 14, 15, 16, 17, 18, 19, or 20 amino acids. A polypeptide, also referred to as a protein, is typically of length≥100 amino acids (Garrett & Grisham, Biochemistry, $2^{nd}$ edition, 1999, Brooks/Cole, 110). A polypeptide, as contemplated herein, may comprise, but is not limited to, 100, 101, 102, 103, 104, 105, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or more amino acid residues. A "protein" generally refers to a polypeptide (or peptide), which optionally may be further modified to include non-amino acid moieties and which exhibits a biological function.

The peptides and polypeptides contemplated herein may be further modified to include non-amino acid moieties. Modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein), Distinct from glycation, which is regarded as a nonenzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine).

The peptides and polypeptides disclosed herein may exhibit at least two-fold, three-fold, four-fold, five-fold, six-fold, seven-fold, ten-fold, twenty-fold, thirty-fold or more increased binding affinity for ZP of oocytes relative to at least one category or type of other cell (e.g. oocytes of target species relative to oocytes of non-target species). Peptides and polypeptide that exhibit such binding characteristics are said to exhibit preferential binding to ZP. Peptides and polypeptides that do not exhibit at least a two-fold increased binding affinity for ZP relative to another category or type of other cell but that bind to ZP are simply said to bind to ZP.

Preferably, the peptides and polypeptides disclosed herein selectively bind to ZP of oocytes of a target species relative to ZP of oocytes of a non-target species. In this regard, the peptides and polypeptides may be referred to as "species-specific." In some embodiments, the species-specific peptides and polypeptides disclosed herein may exhibit at least two-fold, three-fold, four-fold, five-fold, six-fold, seven-fold, ten-fold, twenty-fold, thirty-fold or more increased binding affinity for ZP of oocytes of a target species relative to ZP of oocytes of a non-target species.

Species-specific peptides that mimic sperm surface peptides/proteins and bind to zona pellucida (ZP) at fertilization may be identified by utilizing phage display selection. (See FIGS. 2 and 3). ZP is a glycoproteinaceous protective barrier which surrounds each mammalian oocyte and is essential for sperm-oocyte interaction and, therefore, conception. Immunization with ZP-binding peptides (mimicking sperm antigens) stimulates production of anti-peptide antibodies which act as anti-sperm antibodies. Anti-sperm antibodies can reduce fertility by decreasing sperm motility, by inhibiting the acrosome reaction, or by interfering with sperm-oocyte binding. (See Chamley L W, Clarke G N. Antisperm antibodies and conception. Semin Immunopathol 2007; 29(2):169-184; Suri A. Contraceptive vaccines targeting sperm. Expert Opin Biol Ther 2005; 5(3):381-392; and Suri A. Sperm-based contraceptive vaccines: current status, merits and development. Expert Rev Mol Med 2005; 7(18):1-16).

Also contemplated herein are strategies for species-specific overpopulation control. A strategy for species-specific overpopulation control having three major levels of species-specificity may include: Level 1: species-specific antigen, ZP-binding peptide(s) that mimics sperm cell antigens; Level 2: antigen delivery system, for example, species-specific viral or bacterial vector; and Level 3: species-preferred bait and feeder. (See FIG. 4). Although this Example and FIGS. 4-6 relate to a strategy for swine, this strategy can be modified and adapted for other species of animals.

For Level 1, species-specific ZP-binding peptides may be identified using phage display libraries. (See Samoylova T I, Smith B F. Identification of cell targeting ligands using random peptide-presenting phage libraries. In: Bird C, Smith B F, editors. Genetic Library Construction and Screening: Advanced Techniques and Applications. Heidelberg: Springer-Verlag, 2002: 209-231, the content of which is incorporated by reference in its entirety). Phage display libraries are mixtures of billions of genetically engineered phages which display additional foreign (not of phage origin) peptides on their surfaces. In general, to identify target-binding peptides, a peptide library is first reacted with the target. After that, phage particles not bound to the target are removed by washing steps, and the target-specific phage (bound to the target via displayed peptides) are recovered and amplified. To enrich for the target-specific phage, the whole procedure may be repeated several times (e.g., three or four times). To identify the sequences of the peptides responsible for binding to the target, phage DNAs are isolated, sequenced and translated into peptide sequences. In order to select for peptides that are species-specific, prior to reaction with oocytes of the target species, a phage display library may be reacted with oocytes of non-target species that have close homology with respect to ZP glycoproteins. As shown in FIGS. 5 and 6, to select for peptide antigens that are specific for swine, subtractive selection steps on ZP proteins from species of animals with close homology may be performed prior to selection steps on ZP of porcine oocytes. These species of animals with close homology included cat, dog and cow. (See Conner S J, Lefievre L, Hughes D C, Barratt C L. Cracking the egg: increased complexity in the zona pellucida. Hum Reprod 2005; 20(5):1148-1152). These subtractive steps remove phage that bind to ZP on oocytes of non-target species, including those that are common to the target and non-target species. Subtractive selection steps on oocytes from non-target species may be followed by selection of species-specific phage binding to ZP on porcine oocytes.

For Level 2, oligonucleotide sequences coding for species-specific ZP-binding peptide antigens may be inserted into species-specific viral vectors, bacterial vectors, or other vectors. Here, the vector is used as a delivery mechanism to transfer specific genetic material (oligonucleotide coding a peptide antigen) into host cells. As the result, cells that are transfected with the specific genetic material express the desired peptide which then stimulates an immune response. In addition, immune enhancers may be included in the formulation to improve immunogenicity. Examples of species-specific biological delivery vectors that could be appropriate delivery systems for domestic, feral, or wild animals (e.g., see Hammond J M, Johnson M A. Porcine adenovirus as a delivery system for swine vaccines and immunotherapeutics. Vet J. 2005 January; 169(1):17-27) and strains of *Salmonella* sp. mostly restricted to infecting swine).

For Level 3, the vector vaccine may be incorporated into species-preferred bait. The composition of the bait may be specifically formulated for the target species. As an animal contacts, smells, and eats the bait, it becomes immunized and the immune response to the vaccine blocks fertilization. Additionally, the bait can be distributed in feeders designed to exclude species other than the target species.

Also contemplated herein are "nucleic acid sequences" that encode the disclosed peptides and polypeptides. As used herein, the term "nucleic acid sequence" refers to a nucleotide, oligonucleotide, polynucleotide, or any fragment thereof. As used herein, the term "polynucleotide" refers to a nucleotide polymer. A polynucleotide may encode a peptide or polypeptide as disclosed herein. A polynucleotide may be operably linked to a heterologous promoter sequence as a recombinant polynucleotide. "Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame. A recombinant polynucleotide comprising a polynucleotide operably linked to a promoter sequence may be present in a vector (e.g., a plasmid) which may be utilized to transform a host cell (e.g., where the vector further includes a selectable marker). Accordingly, the disclosed peptides and polypeptides may be expressed in a host cell via an encoding nucleic acid sequence.

The peptides and polypeptides may be expressed via vectors that include viral, bacterial, or other vectors. Preferably, the peptide or polypeptides are expressed via a recombinant filamentous bacteriophage (i.e., Ff class bacteriophages). Bacteriophages (or phages) are viruses that infect bacteria. They consist of an outer protein capsid enclosing genetic material (single stranded circular DNA). Filamentous phages (Ff class) are long (~1 μm) and thin (~7 nm) particles. Such particles can be genetically re-engineered and utilized as carriers for immunogenic peptides, which are displayed on phage surfaces as fusion molecules to phage coat proteins. (See Minenkova et al., Gen. 1993:85-88; and Yip et al., Immunol. Lett. 2001 Dec. 3; 79(3):197-202). To create fusion peptides, a foreign oligonucleotide usually is inserted into the phage minor coat protein gene 3 or the phage major coat protein gene 8. Inserts in gene 3 produce fusions with a maximum of 5 copies of protein III (pIII). Inserts in gene 8 produce multiple fusion peptides, the number of which depends on the phage vector design. Usually, protein VIII (pVIII) vectors contain two copies of gene 8, one of which encodes the wild-type protein, and the other encodes a fusion protein. Such vector design results in irregular phage surface architecture that contains a variable number (from 15 to 300) of fusion peptides separated by wild-type phage proteins. However, by using a bacteriophage vector that has only one copy of gene 8, all copies of the major coat protein VIII are modified with the fusion peptide. (Sec Petrenko et al., Protein Eng. 1996 September; 9(9):797-801). Such a bacteriophage may otherwise be referred to as a "landscape phage" in view of the dramatic change in surface structure of the phage caused by the >1000 copies of the heterologous peptide present in a dense, repeating pattern on the phage's tubular capsid. In landscape phage, foreign peptides are expressed in each copy of the phage major coat protein VIII, resulting in a surface density of as many as 4000 foreign peptide copies per phage particle. (See FIG. 1). Most importantly, high density epitopes in the landscape phage are presented in a highly-organized manner and are properly spaced for binding to B cell receptors. Such repetitive highly-organized epitope patterns usually permit a cross-linking activation of B-cell receptors, which provides robust, long-lasting immune responses. (See Bachmann et al., Annu. Rev. Immunol. 1997; 15:235-70; and Fehr et al., Proc. Natl. Acad. Sci. USA 1998 Aug. 4; 95(16):9477-81). Additionally, phage are able to stimulate strong T helper cell responses. (See Gaubin et al, DNA Cell Biol. 2003 January; 22(1):11-18; Hashemi et al., J. Virol. Methods 2010 February; 163(2):440-444; Ulivieri et al., Immunol. Lett. 2008 Aug. 15; 119(1-2):62-70; and Wan et al., Eur. J. Immunol. 2005 July, 35(7:2041-50). Phage particulate nature, size and shape further appeal for its strong/long-lasting immunogenic potentials. Filamentous phage has been shown to naturally stimulate both B and T helper cell responses without adjuvants. (See De Berardinis et al., Expert Rev. Vaccines 2004 December; 3(6):673-9; and Manoutcharian et al., Curr. Pharm. Biotechnol. 2001 September; 2(3): 217-23). Although they can not infect animal cells, landscape phage may be inactivated prior to subsequent use in an immunogenic or vaccine composition.

Phages, as bacterial viruses, can be easily obtained in large quantities from bacterial cultures, which makes the cost of phage preparations much lower than the cost of peptides vectored in mammalian viruses or the cost of production of synthetic peptides. Importantly, landscape phage preparations are very thermostable. They resist degradation and retain antigenicity for more than six months at room temperature, more than six weeks at 63° C., and three days at 76° C. (see Brigati et al., Anal. Bioanal. Chem. 2005 July, 282(6): 1346-50), making landscape phage-based preparations ideally suited for shipping, storage, and delivery in field conditions without requiring refrigeration. Examples of phage-based (non-landscape phage) vaccines reported in the literature include preparations for treatment of melanoma (Eriksson et al., Cancer Immunol. Immunother. 2007 May; 56(5):677-87; and Eriksson et al., J. Immunol. 2009 Mar. 1; 182(5):3105-11), HIV (see De Berardinis et al., Curr. HIV Res. 2003 October; 1(4):441-6), Alzheimer's disease (see Frenkel et al. Vaccine 2003 Mar. 7; 21(1'-12):1060-5), candidiasis (see Wang et al., Vaccine 2006 Aug. 28; 24(35-36): 6065-73; and Yang et al., Mycoses 2007 May; 50(3):165-71), and rabies (see Houimel et al., Vaccine 2009 Jul. 23; 27(34): 4648-55). Furthermore, recombinant phages displaying decapeptides of follicle-stimulating hormone receptor were shown to impair fertility in mice and inhibit ovulation rates in ewes (see Abdennebi et al., J. Mol. Endocrinol. 1999 April; 22(2):151-9) and to induce infertility in adult male bonnet monkeys (see Rao et al., Reprod. Biomed. Online 2004 April; 8(4):385-91), suggesting the potential use of phage-based vaccines for immunocontraception. These vaccines were shown to stimulate anti-peptide responses with only 5 to 300 peptide copies (irregularly spaced) per phage particle, stimulating both systemic and mucosal immunity. Filamentous phage preparations based on fd phage (same as landscape phage) have been used experimentally in humans with the approval of the FDA and with no apparent side effects (see Krag et al., Cancer Res. 2006 Aug. 1; 66(15): 7724-33), indicating their safety.

Recombinant phage particles displaying fusion peptides can be obtained via cloning of oligonucleotides encoding for the fusion peptides in phage display vectors. Alternatively, phage clones displaying desired peptides or their structural/functional mimics can be selected from phage display libraries.

The presently disclosed peptides, polypeptides, landscape phage, or vectors may be isolated or substantially purified. The terms "isolated" or "substantially purified" refers to peptides, polypeptides, landscape phage, or vectors that have been removed from a natural environment and have been isolated or separated, and are at least 60% free, preferably at least 75% free, and most preferably at least 90% free from other components with which they were naturally associated.

Also disclosed are peptide and polypeptides identified by the phage display method, and preferably include species-specific ZP-binding peptide and polypeptides. Peptides identified herein include peptides having the amino acid sequence or motifs of SEQ ID NOS:1-56. Also disclosed are polypeptides comprising the amino acid sequence or motifs of any of SEQ ID NOS:1-56, polynucleotides encodings such polypeptides, recombinant polynucleotides comprising such polynucleotides, expression vectors, and methods for expressing the encoded polypeptide.

The peptides disclosed herein may be fused or conjugated to one or more other peptides or non-peptide moieties (e.g., in order to provide an antigen). For example, a fusion polypeptide as contemplated herein may include a fusion of any of the peptides or motifs of SEQ ID NO:1-56 and one or more other immunogenic peptides. The peptides disclosed herein may be present in a polypeptide (e.g., where the polypeptide comprises one or more copies of the amino acid sequence of the peptide, optionally in tandem). The disclosed peptides may be modified to enhance immunogenicity. For example, the peptides disclosed herein may be conjugated to one or more carrier proteins (e.g., keyhole-limpet hemocyanin).

The disclosed methods may include inducing an immune response against one or more peptides that bind to the ZP (e.g., an immune response against one or more species-specific peptides that bind to the ZP). In some embodiments, the methods include inducing polyclonal antibodies against one or more peptides that bind to the ZP by administering to an animal an immunogenic composition that includes one or more of the peptides (and preferably, one or more specific peptides) or that includes one or more vectors that express one or more of the peptides. The animal may be a non-human mammal. The induced polyclonal antibodies may include anti-sperm antibodies. The methods disclosed herein also may include preventing conception by administering to the animal an immunogenic composition that includes one or more peptides that bind to the ZP (and preferably, one or more specific peptides that bind to the ZP) or that includes one or more vectors that express one or more of the peptides. For example, an animal (e.g., a non-human mammal) may be protected against conception by administering to the animal a composition that includes one or more peptides that bind to the ZP or that includes one or more vectors that express one or more peptides that bind to the ZP together with a suitable excipient.

The disclosed compositions may be administered as immunogenic compositions or vaccines utilizing a selected "prime-boost vaccination regimen." As used herein, a "prime-boost vaccination regimen" refers to a regimen in which a subject is administered a first composition one or more times (e.g., one time or two or three times with about 2, 3, or 4 weeks between administrations) and then after a determined period of time after having administered the first composition (e.g., about 2 weeks, about 4 weeks, about 2 months, about 3 months, about 4 months, about 5 months, about 6 months, or longer), the subject is administered a second composition. The second composition may also be administered more than once, with at least 2, 3, or 4 weeks between administrations. The first and second compositions may be the same or different.

Also disclosed are immunogenic compositions and vaccines for performing the disclosed methods. The immunogenic or vaccine compositions may comprise any one or more of: (1) the presently disclosed peptides and polypeptides; (2) nucleic acid sequences encoding the disclosed peptides and polypeptides; (3) landscape phage comprising the disclosed peptides and polypeptides; and (4) other viral or bacterial vectors that express the disclosed peptides and polypeptides. The disclosed immunogenic or vaccine compositions may be monovalent or polyvalent. Typically, the immunogenic compositions include one or more peptides that bind to the ZP (e.g., species-specific ZP-binding peptides), or the immunogenic compositions include one or more vectors that express one or more peptides that bind to the ZP (e.g., species-specific vectors that express species-specific ZP-binding peptides). For example, the immunogenic compositions may include one or more landscape phage that express one or more peptides that bind to the ZP. The immunogenic compositions also may include a suitable excipient, carrier, or diluent.

Suitable peptides for the immunogenic compositions (or for expression by vectors of the immunogenic compositions) may include one or more polypeptides comprising the amino acid sequence of a peptide as disclosed herein, for example one or more polypeptides comprising the amino acid sequence or motifs of any of SEQ ID NOS:1-56. In some embodiments, the immunogenic compositions may include two or more polypeptides (or two or more vectors that express two or more polypeptides) where each polypeptide of the two or more polypeptides comprises the amino acid sequence or motifs of any of SEQ ID NOS:1-56. The immunogenic compositions may include an isolated polypeptide or peptide at a concentration sufficient to induce an immunogenic response against sperm (e.g., via antibody induction, a T-cell response, or both), or the immunogenic compositions may include one or more vectors that express the polypeptide or peptide at a concentration sufficient to induce an immunogenic response against sperm (e.g., via antibody induction, a T-cell response, or both). In some embodiments, the immunogenic compositions may include at least about 10 µg of the isolated polypeptide or peptide (or preferably, at least about 100 µg of the isolated polypeptide or peptide).

The "immunogenic compositions" and "vaccines" disclosed herein are capable of stimulating an immune response in an animal inoculated with the immunogenic composition or vaccine. An immune response may include induction of antibodies, induction of a T-cell response, or both. Herein, the term "prevention" when used in reference to an immunogenic composition or vaccine may refer to the partial or complete prevention against conception via an immune response induced by the immunogenic composition or vaccine.

An "an immunogenic composition comprising a given peptide or polypeptide" refers to a composition containing the given peptide or polypeptide. The composition may comprise a dry formulation or an aqueous solution. An "immunogenic peptide or polypeptide" is an antigen which is capable of eliciting an immune response when introduced into an animal, for example, a non-human mammal.

The methods disclosed herein may include administering an immunogenic composition or a vaccine to an animal. An "animal," as used herein, may include a non-human mammal.

The methods disclosed herein also may include protecting an animal against conception or preventing an animal from conceiving by administering to the animal a composition (e.g., a bait composition) that includes an isolated peptide as disclosed herein or that includes a vector that expresses the peptide. The administered composition may include an immunogenic composition or a vaccine composition. For example, an animal may be protected against conception by administering to the animal a bait composition that includes an isolated polypeptide comprising an amino acid sequence or motif of any of SEQ ID NOS:1-56 or a vector that expresses a polypeptide comprising an amino acid sequence or motif of any of SEQ ID NOS:1-56. The compositions disclosed herein may further include a suitable excipient, carrier, or diluent.

In some embodiments, the disclosed peptides or polypeptides may be expressed by a vector other than a landscape phage, for example animal virus vectors or bacterial vectors (e.g., as included as part of an immunogenic composition, vaccine, or bait composition). As used herein, an "animal viral vector" refers to recombinant animal virus nucleic acid that has been engineered to express a heterologous polypeptide. The recombinant animal virus nucleic acid typically includes cis-acting elements for expression of the heterologous polypeptide. The recombinant animal virus nucleic acid typically is capable of being packaged into a helper virus that is capable of infecting a host cell. For example, the recombinant animal virus nucleic acid may include cis-acting elements for packaging. Typically, the animal viral vector is not replication competent or is attenuated. An "attenuated recombinant virus" refers to a virus that has been genetically altered by modern molecular biological methods (e.g., restriction endonuclease and ligase treatment, and rendered less virulent than wild type), typically by deletion of specific genes. For example, the recombinant animal virus nucleic acid may lack a gene essential for the efficient production or essential for the production of infectious virus. Suitable animal viral vectors for expressing the peptides and polypeptides disclosed herein may include, but are not limited to adenovirus vectors, Sendai virus vectors, and measles virus vectors. Recombinant attenuated bacteria also may be utilized as vectors in the pharmaceutical compositions and vaccines disclosed herein (e.g., recombinant attenuated *Shigella, Salmonella, Listeria,* or *Yersinia*). Recombinant bacterial vaccine vectors are described in Daudel et al., "Use of attenuated bacteria as delivery vectors for DNA vaccines," Expert Review of Vaccines, Volume 6, Number 1, February 2007, pp. 97-110(14); Shata et al., "Recent advances with recombinant bacterial vaccine vectors," Molec. Med. Today (2000), Volume 6, Issue 2, 1 Feb. 2000, pages 66-71; Clare & Dougan, "Live Recombinant Bacterial Vaccines," Novel Vaccination Strategies, Apr. 16, 2004 (Editor Stefan H. E. Kaufman); Gentschev et al., "Recombinant Attenuated Bacteria for the Delivery of Subunit Vaccines," Vaccine, Volume 19, Issues 17-19, 21 Mar. 2001, Pages 2621-2628; Garmory et al., "The use of live attenuated bacteria as a delivery system for heterologous antigens," J. Drug Target. 2003; 11(8-10):471-9; U.S. Pat. No. 6,383,496; and U.S. Pat. No. 6,923,958 (which all are incorporated by reference herein in their entireties). Preferably, the vector is species-specific, whereby the vector selectively infects a target species of animal or the vector selectively expresses an encoded heterologous peptide in the target species of animal after infecting the animal.

The immunogenic compositions or vaccines may be formulated for delivery in any suitable manner. For example, the immunogenic compositions or vaccines may be formulated for at least one of oral delivery, intranasal delivery, intramuscular delivery, subdermal delivery, subcutaneous delivery, intravenous delivery, and intraperitoneal delivery. The immunogenic compositions or vaccines can be administered using a variety of methods including intranasal and/or parenteral (e.g., intramuscular) administration. In some embodiments of the methods, the immunogenic composition or vaccine is administered intramuscularly one or more times at suitable intervals (e.g., at intervals of 2-4 weeks), followed by administration of the immunogenic composition or vaccine at least once intramuscularly or intranasally after a suitable time period (e.g., 2-4 weeks after the last parenteral administration of vaccine). The immunogenic compositions or vaccines may be administered to an animal of either sex. In some embodiments, the animal is female.

The present immunogenic composition and vaccines may be formulated with a pharmaceutically or veterinarily acceptable excipient, carrier, or diluent. The forms suitable for injectable commonly include sterile aqueous solutions (where water soluble) or dispersions and sterile powders for the extemporaneous preparation of sterile injectable solutions or dispersion. The formulation should desirably be sterile and fluid to the extent that easy syringability exists. The dosage form should be stable under the conditions of manufacture and storage and typically is preserved against the contaminating action of microorganisms such as bacteria and fungi. The carrier can be a solvent or dispersion medium containing, for example, water, ethanol, polyol (for example, glycerol, propylene glycol, liquid polyethylene glycol, and the like), suitable mixtures thereof and vegetable oils. One possible carrier is a physiological salt solution. The proper fluidity of the solution can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal (sodium ethylmercuri-thiosalicylate), deomycin, gentamicin and the like. In many cases it may be preferable to include isotonic agents, for example, sugars or sodium chloride. Prolonged absorption of the injectable compositions, if desired, can be brought about by the use in the compositions of agents delaying absorption, for example, aluminum monostearate and gelatin.

The present immunogenic composition or vaccines may include an adjuvant. The term "adjuvant" refers to a compound or mixture that is present in an immunogenic composition or vaccine and enhances the immune response to an antigen present in the immunogenic composition or vaccine. For example, an adjuvant may enhance the immune response to a polypeptide present in a vaccine as contemplated herein, or to an immunogenic fragment or variant thereof as contemplated herein. An adjuvant can serve as a tissue depot that slowly releases the antigen and also as a lymphoid system activator that non-specifically enhances the immune response. Examples of adjuvants which may be employed include MPL-TDM adjuvant (monophosphoryl Lipid A/synthetic trehalose dicorynomycolate, e.g., available from GSK Biologics). Another suitable adjuvant is the immunostimulatory adjuvant AS021/AS02 (GSK). These immunostimulatory adjuvants are formulated to give a strong T cell response and include QS-21, a saponin from *Quillay saponaria*, the TL4 ligand, a monophosphoryl lipid A, together in a lipid or liposomal carrier. Other adjuvants include, but are not limited to, nonionic block co-polymer adjuvants (e.g., CRL1005), aluminum phosphates (e.g., $AlPO_4$), R-848 (a Th1-like adjuvant), imiquimod, PAM3CYS, poly (1:C), loxoribine, potentially useful human adjuvants such as BCG (bacille Calmette-Guerin) and *Corynebacterium parvum*, CpG oligodeoxynucleotides (ODN), cholera toxin derived antigens (e.g., CTA1-DD), lipopolysaccharide adjuvants, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions in water (e.g., MF59 available from Novartis Vaccines or Montanide ISA 720), keyhole limpet hemocyanins, and dinitrophenol.

It is generally advantageous to formulate the present compositions in dosage unit form for ease of administration and uniformity of dosage. "Dosage unit form" as used herein refers to physically discrete units suited as unitary dosages for the animal subjects to the treated; each unit containing a predetermined quantity of the active material calculated to produce the desired therapeutic effect in association with the required pharmaceutical carrier. The specification for the dosage unit forms are dictated by and depend on among other factors (a) the unique characteristics of the active material and the particular therapeutic effect to be achieved; (b) the limitations inherent in the art of compounding such active material for the treatment of disease; and (c) the manner of intended administration of the dosage unit form. In some embodiments, a dose of the immunogenic composition or vaccine includes at least about 10 micrograms (preferably 100 micrograms) of one or more isolated polypeptides or peptides as disclosed herein.

Sterile injectable solutions may be prepared by incorporating the isolated polypeptide or peptide in the desired amount in an appropriate solvent with various of the other ingredients enumerated above, as required, followed by filtered sterilization. Generally, dispersions can be prepared by incorporating the various active ingredients into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yield a powder of the active ingredient (i.e., lyophilized form of the active ingredient) plus any additional desired ingredient from a previously sterile-filtered solution thereof.

It also may be advantageous to add a stabilizer to the present compositions. Suitable stabilizers include, for example, glycerol/EDTA, carbohydrates (such as sorbitol, mannitol, trehalose, starch, sucrose, dextran or glucose), proteins (such as albumin or casein) and protein degradation products (e.g., partially hydrolyzed gelatin). If desired, the formulation may be buffered by methods known in the art, using reagents such as alkali metal phosphates, e.g., sodium hydrogen phosphate, sodium dihydrogen phosphate, potassium hydrogen phosphate and/or potassium dihydrogen phosphate. Other solvents, such as ethanol or propylene glycol, can be used to increase solubility of ingredients in the vaccine formulation and/or the stability of the solution. Further additives which can be used in the present formulation include conventional antioxidants and conventional chelating agents, such as ethylenediamine tetraacetic acid (EDTA).

The disclosed immunogenic composition, vaccine compositions, and the peptide or expression vectors included therein may be formulated as a species-specific bait composition (e.g., as a contraceptive species-specific bait vaccine). The disclosed compositions also may include bait compositions for attracting a target species of animal. The bait compositions may include ZP-binding peptides (e.g., as disclosed herein), vectors that express the ZP-binding peptides, immunogenic compositions that include ZP-binding peptides, or vaccine compositions that include the ZP-binding peptides. The bait compositions thereof may be specific-specific in one or more aspects, including but not limited to: (1) the bait compositions attract a target species of animal and do not attract a non-target species of animal; (2) the bait compositions comprise a species-specific vector (e.g., a viral vector that specifically infects a target species of animal or that is capable of replicating or expressing an encoding protein only in a target species of animal and not a non-target animal); (3) the bait composition comprises species-specific ZP-binding peptides or polypeptides or comprises vectors that express species-specific ZP-binding peptides or polypeptides. The bait composition is formulated to attract a target species (e.g., a feral pig or dog) and is formulated not to attract non-target species of animals (e.g., birds). The bait composition may be flavored, colored, or scented, in order to selectively attract a target species while not attracting or only minimally attracting a non-target species of animal. Ingredients that may be used in the bait composition may include, but are not limited to, cereals or grains (e.g., barley), fish (or fish flavoring), meat (or meat flavoring), vegetables (e.g., potatoes), fruits (e.g., apples), dairy products (e.g., milk or milk powder), and oils (e.g., vegetable oil or fish oil). Feral pig bait compositions are known in the art (see, e.g., PIGOUT® brand feral pig bait (Animal Control Technologies, Somerton, Victoria AU)) and have been utilized for oral vaccination of feral pigs (see, e.g., Ballestreros et al., "Evaluation of baits for oral vaccination of European wild boar piglets," Res. Vet. Sci. 2008 Oct. 22 epub; Cowled et al., "Vaccination of feral pigs (*Sus scrofa*) using iophenoxic acid as a simulated vaccine," Aust. Vet. J. 2008 January-February; 86(1-2):50-5; and Kaden et al., "Oral immunisation of wild boar against classical swine fever: evaluation of the first field study in Germany," Vet. Micro., April 2000, 73(2-3):239-252, which contents are incorporated herein by reference in their entireties).

The disclosed compositions, which may include bait compositions, may be administered to a target species of animal. As contemplated herein, "administering" a composition to an animal may include feeding a bait composition to the animal or depositing a bait composition in locations where the animal is likely to come in contact with the bait composition and smell, touch, taste, or eat the bait composition.

Also disclosed herein are isolated antisera, antibodies, or other binding molecules that bind specifically to the peptides disclosed herein. For example, the antisera, antibodies, or other binding molecules, may include an isolated antibody that binds specifically to a polypeptide consisting of an amino acid sequence or motif of any of SEQ ID NOS:1-56. Preferably, the antisera, antibodies, or other binding molecules disclosed herein also bind specifically to sperm. The isolated antibody or binding molecule may be of any suitable isotype (e.g., IgG, IgM, IgE, IgD, IgA, and mixtures thereof). The antibodies may be polyclonal or monoclonal. The term "antibody or other binding molecule" refers to intact immunoglobulin molecules as well as to fragments thereof, such as Fab, $F(ab')_2$, and Fv fragments, which are capable of binding an epitopic determinant. The antibodies or other binding molecules may be naturally occurring or synthetic (e.g., scFv). Other binding molecules may include antibody fragments (e.g., Fab fragments), coupled antibodies, and coupled antibody fragments. Antibodies or other binding molecules that bind the presently disclosed peptides and polypeptides can be induced or elicited using the intact peptide or a polypeptide comprising the intact peptide as an immunizing antigen. The polypeptide or oligopeptide used to immunize an animal can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide may then be used to immunize the animal. The antibodies or other specific binding molecules may be conjugated to a suitable therapeutic agent (e.g., a toxin) or a label. The antibodies may be modified for use in therapeutic or diagnostic methods.

Also disclosed herein are kits. The kits may include one or more components for performing the methods disclosed herein. For example, the kits may include one or more of the immunogenic compositions or vaccines for immunizing or vaccinating an animal, where the immunogenic compositions or vaccines optionally are formulated as species-specific bait compositions. The disclosed kits may include components for making the immunogenic compositions or vaccines as disclosed herein, or for formulating bait compositions comprising the immunogenic compositions or vaccines. The components of the disclosed kits may be provided in any suitable form (e.g., liquid form or lyophilized form). Kits further may include solvents for resuspending or dissolving a lyophilized protein.

EXAMPLES

The following Examples are illustrative and are not intended to limit the scope of the claimed subject matter.

Example 1

Identification of Peptides that Bind Pig Oocyte ZP

Figure 3:
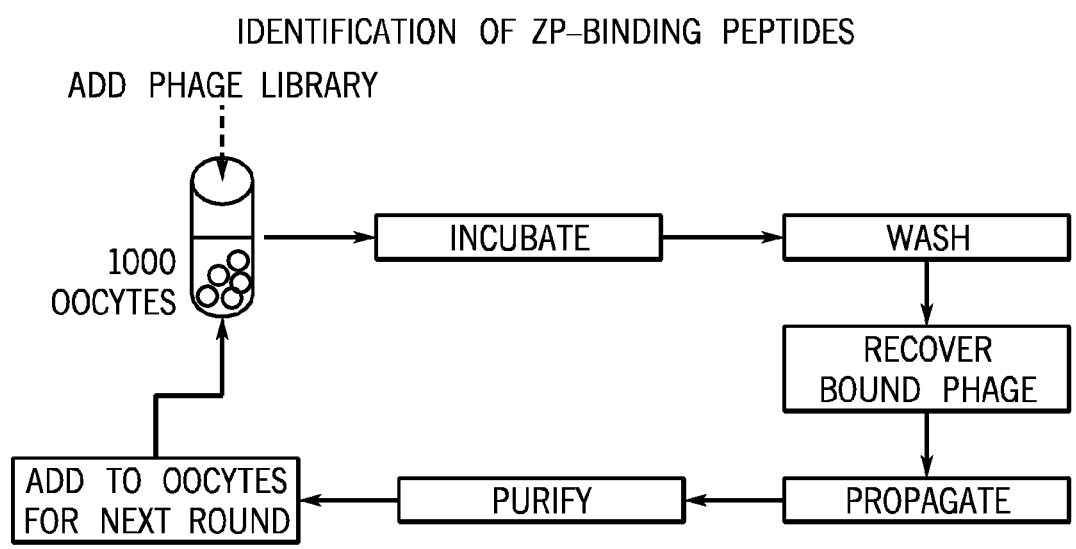
FIG. 3. illustrates a method for identifying ZP-binding peptides.

As previously described in U.S. Published Application No. 2011-0044989, published on Feb. 24, 2011 (the content of which is incorporated herein by reference in its entirety), peptides that bind to ZP glycoproteins on intact pig oocytes were identified using PhD-12 Phage Display Peptide Library purchased from New England BioLabs. The utilized approach selected peptides that mimic the sperm antigen at the level of the ZP-sperm binding. For Example 1, three rounds of selection were performed on pig oocytes. Pig oocytes and oocytes of non-target species (i.e., cat, dog, and cow oocytes as utilized in Example 2) were obtained utilizing a modification of the method disclosed by Dunbar et al. (Biol. Reprod. 1980; 22:941-954). In the first selection round, an aliquot of the primary library was diluted in a blocking buffer and incubated with 1000 intact pig oocytes surrounded by ZP (FIG. 3). After incubation, phage expressing peptides not bound to ZP were washed away and the bound phage were recovered by incubation with a lysis buffer. Two additional selection rounds were performed similarly. Translation of foreign oligonucleotide inserts in phage DNA revealed sequences of the peptides that were responsible for binding to pig oocyte ZP. Peptide sequences from the phage display selection on intact pig oocytes surrounded by ZP are shown in FIG. 7. These peptide sequences which bind to pig oocyte ZP may or may not be species-specific. For example, these identified peptide sequence may bind to conservative regions of ZP glycoproteins that are common to multiple species of animals.

Example 2

Identification of 12-Mer Peptides that Bind Specifically to Pig Oocyte ZP

Figure 6:
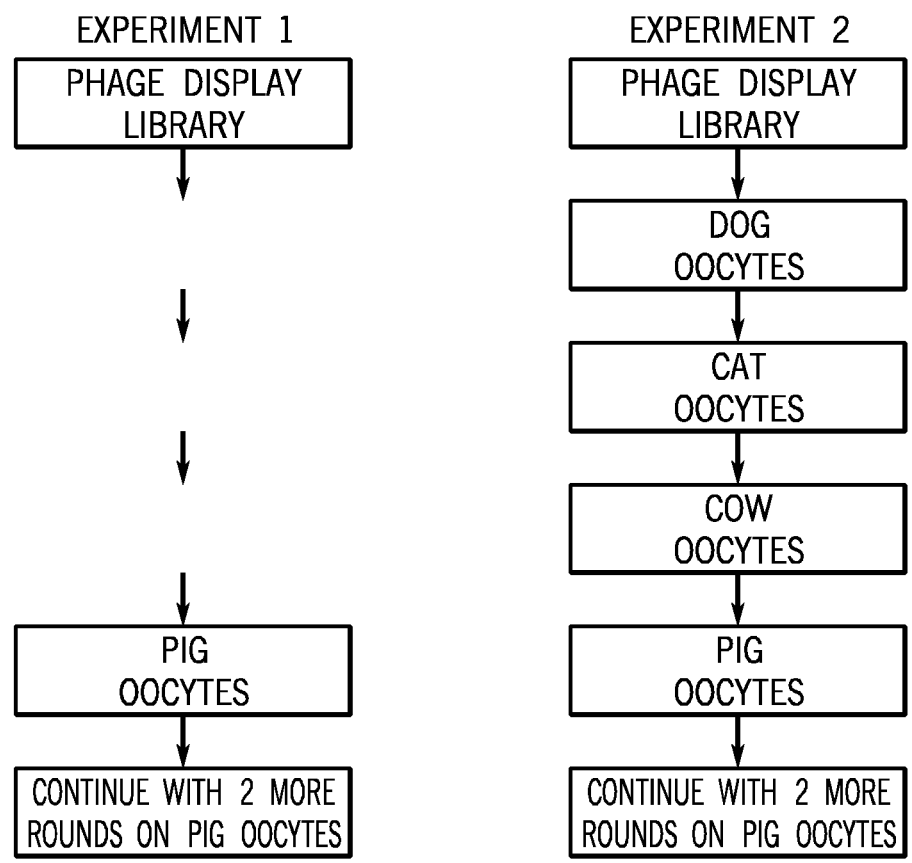
FIG. 6. provides schematics of the experiments described in Examples 1 and 2.

As previously described in U.S. Published Application No. 2011-0044989, published on Feb. 24, 2011 (the content of which is incorporated herein by reference in its entirety), peptides that bind only to ZP proteins on pig oocytes (pig-specific peptides) were identified. (See FIGS. 5 and 6.) Prior to reaction with pig oocytes, PhD-12 Phage Display Peptide Library was reacted with oocytes of non-target species (cat, dog, and cow oocytes) that have close homology to pig oocytes with respect to ZP proteins. (See Conner S J, Lefievre L, Hughes D C, Barratt C L. Cracking the egg: increased complexity in the zona pellucida. Hum Reprod 2005; 20(5): 1148-1152). For each of these subtractive selection steps, 2000 oocytes with ZP from each non-target species were used. Subtractive selection steps were followed by three rounds of selection on pig oocytes (1000 oocytes per round). In each round, phage expressing peptides not bound to ZP of oocytes were washed away and the bound phage were recovered by incubation with lysis buffer. Translation of foreign oligonucleotide inserts in phage DNA revealed sequences of the peptides that were responsible for binding specifically to ZP proteins on pig oocytes. Peptide sequences from phage display selection on intact pig oocytes surrounded by ZP are shown in FIG. 8. Peptide sequences identified in Example 2 are pig-specific. Comparative analysis indicates that peptide sequences shown in FIGS. 7 and 8 are different (with the exception of the peptide of SEQ ID NO:2), indicating that peptides common for dog, cat, cow and swine were removed in pre-selection procedures on dog, cat and cow oocytes prior to the three rounds of selection on pig oocytes.

Example 3

Immunogenicity of 12-Mer Peptides that Bind to Pig Oocyte ZP

Figure 9:
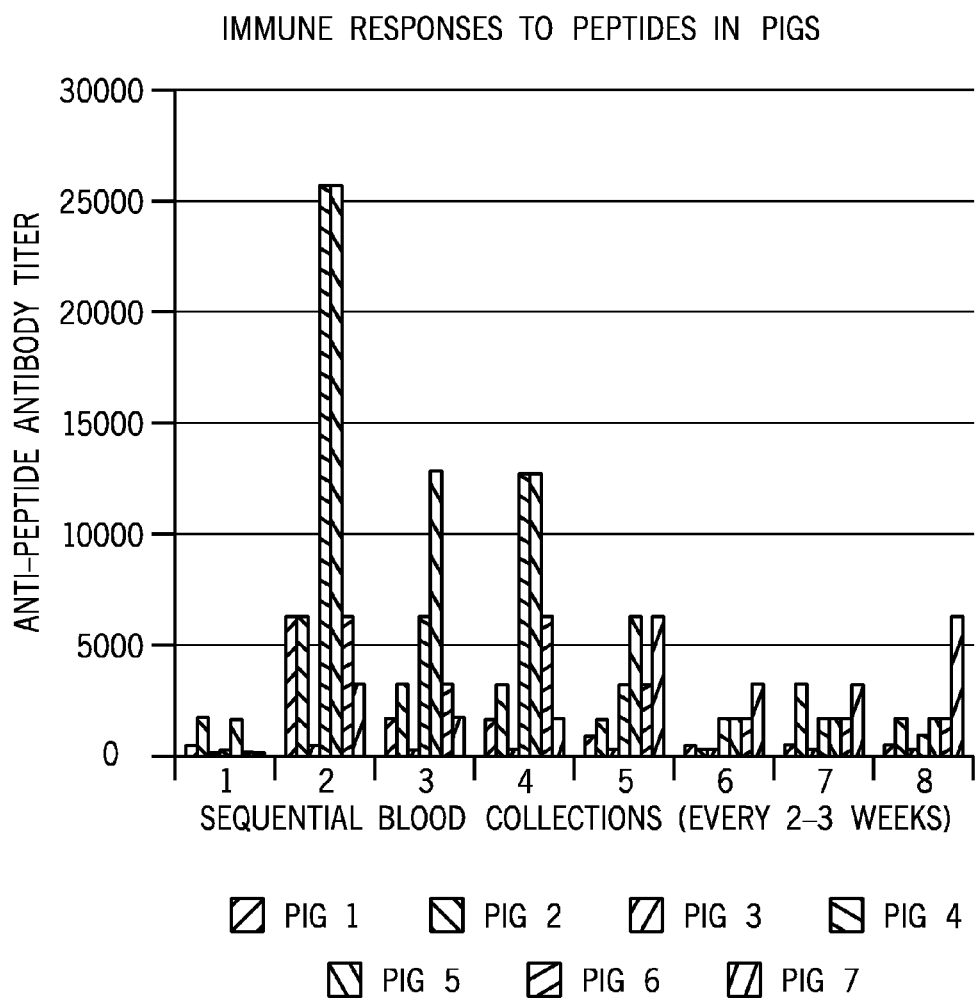
FIG. 9. illustrates anti-peptide antibody responses in pigs immunized with synthetic peptides conjugated to a carrier protein. The peptide sequences were: 1. YLPVGGLRRIGG (SEQ ID NO:57) (control from literature); 2. YMPNPFTASKWK (SEQ ID NO:8)—Ex. 1; 3. AVTQHLKFKGFN (SEQ ID NO:21)—Ex. 2; 4. LLADTTHHRPWT (SEQ ID NO:19)—Ex. 2; 5. TLGWTANEAPRR (SEQ ID NO:18)—Ex. 2; 6. DANRLPHPANIN (SEQ ID NO:2)—Ex. 1, Ex. 2; and 7. SQSPAMYSQTRP (SEQ ID NO:20)—Ex. 2.

Six of the peptides identified in Examples 1 and 2 and one control peptide were synthesized and conjugated to a carrier protein (FIG. 9). The peptide sequences were: 1. YLPVGGL-RRIGG (SEQ ID NO:57) (control from literature); 2. YMP-NPFTASKWK (SEQ ID NO:8)—Example 1; 3. AVTQHLK-FKGFN (SEQ ID NO:21)—Example 2; 4. LLADTTHHRPWT (SEQ ID NO:19)—Example 2; 5. TLG-WTANEAPRR (SEQ ID NO:18)—Example 2; 6. DANRL-PHPANIN (SEQ ID NO:2)—Example 1 and Example 2; and 7. SQSPAMYSQTRP (SEQ ID NO:20)—Example 2. These constructs were injected into domestic pigs and blood samples collected for four months to evaluate antibody responses. Two of the candidate peptides elicited high titers (≥1:25,600) of anti-peptide antibodies detected at five weeks post-primary injection (FIG. 9).

Example 4

Identification of 9-Mer Peptides that Bind Specifically to Pig Oocyte ZP Using a Landscape Phage Library Using a strategy similar to the strategy of Example 2, 9-mer peptides that bind specifically to pig oocyte ZP were identified using a landscape phage library. In this library, foreign (non-phage) 9-mer peptides are expressed in each pVIII copy over the phage surface resulting in thousands of peptide copies per phage particle. Using selections on pig oocytes with intact zona pellucida, multiple peptides that specifically recognize and bind to pig ZP were identified. Prior to phage display library selection on pig oocytes, negative selection steps on cat, dog and cow oocytes were performed. Sequences of the identified peptides are DPGLSLGDD (SEQ ID NO:41); AYNLGEGDT (SEQ ID NO:42); GQQGLNGDS (SEQ ID NO:43); DVGGGTGTE (SEQ ID NO:44); GPNSS-DADS (SEQ ID NO:45); and GEGGYGSHD (SEQ ID NO:46).

Example 5

Methods, Compositions, and Sequences of ZP-Binding Peptides for Immunocontraception of Dogs and Other Animals Reference is made to U.S. Published Application No. 2009-0280137, published on Nov. 12, 2009, and Samoylova et al., Anim. Reprod. Sci. 2010 July, 120(1-4):151-7, the contents of which are incorporated herein by reference in their entireties.

Example 6

Identification of 9-Mer Peptides that Bind to Dog Oocyte ZP Using a Landscape Phage Library Using a strategy similar to the strategy of Examples 2 and 5, 9-mer peptides that bind to dog oocyte ZP were identified using a landscape phage library. In this library, foreign (non-phage) 9-mer peptides are expressed in each pVIII copy over the phage surface resulting in thousands of peptide copies per phage particle. Using selections on dog oocytes with intact zona pellucida, multiple peptides that specifically recognize and bind to dog ZP were identified. Sequences of the identified peptides are DDLNSFVND (SEQ ID NO:47); ADLAAFYDD (SEQ ID NO:48); EPGGMVGSD (SEQ ID NO:49); DGVYLVGDD (SEQ ID NO:50); DWSGQDVEN (SEQ ID NO:51); and GMVGSGYDS (SEQ ID NO:52).

Example 7

Immunogenicity of 9-Mer Peptides that Bind to Dog Oocyte ZP

Figure 10:
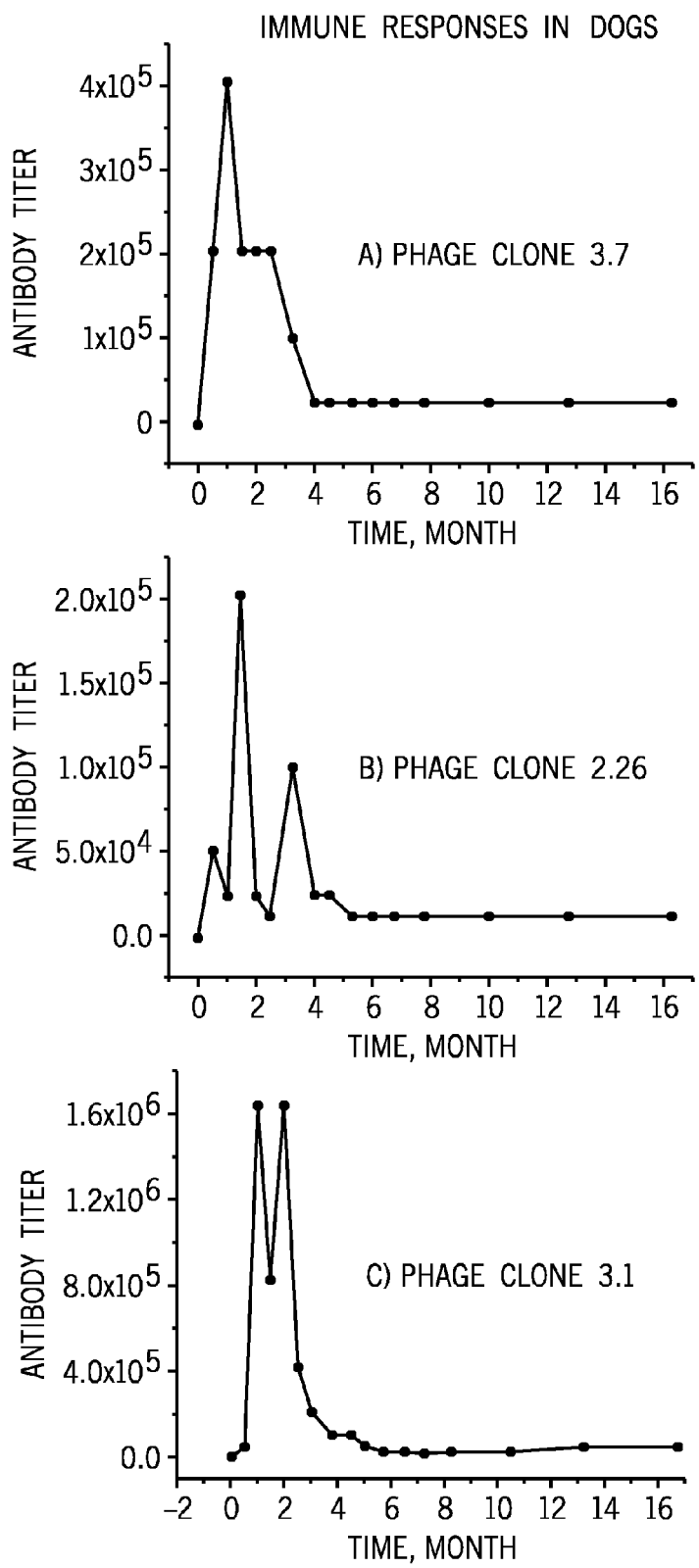
FIG. 10. illustrates anti-peptide antibody responses in dogs immunized with whole landscape phage particles carrying the following peptides: a) phage clone 3.7—EPGGMVGSD (SEQ ID NO:49); b) phage clone 2.26—EVNGGSADS (SEQ ID NO:54); and c) phage clone 3.1—DDLNSFVND (SEQ ID NO:47).

Contraceptive vaccines comprising landscape phage having three different dog oocyte ZP-binding peptides identified in Example 6 were injected intramuscularly into one-year old male dogs (FIG. 10). The whole landscape phage particles carried the following peptides: a) phage clone 3.7—EPGGM-VGSD (SEQ ID NO:49); b) phage clone 2.26—EVNGGSADS (SEQ ID NO:54); and c) phage clone 3.1—DDLNSFVND (SEQ ID NO:47). As such, in these vaccines, the phage body functions as a carrier protein for the multiple peptide copies. Booster immunizations were given at 3 weeks and again at 7 weeks following initial immunization. Sera collected from immunized dogs were characterized as to the presence of anti-peptide/anti-sperm antibodies as well as testosterone levels and size of testicles (FIG. 11). All phage preparations were shown to induce production of high levels of serum IgG antibodies that persisted for at least 10-12 months. Testosterone levels varied during the study showing some decrease (with the lowest testosterone amount of 0.3 ng/ml) in two dogs after booster immunizations. Interestingly, testicular widths in all dogs were decreased when measured 2-3 months after the second booster immunizations. In conclusion: (1) landscape phage-peptide preparations injected intramuscularly (even at high doses of 500 µg) do not cause any side effects, either local or systemic, and (2) landscape phage-peptide constructs are immunogenic and stimulate production of anti-peptide antibodies at high titers.

Example 8

Identification of 9-Mer Peptides that Bind to Cat Oocyte ZP Using a Landscape Phage Library Using a strategy similar to the strategy of Examples 2, 5, and 7, 9-mer peptides that bind to cat oocyte ZP were identified using a landscape phage library. In this library, foreign (non-phage) 9-mer peptides are expressed in each pVIII copy over the phage surface resulting in thousands of peptide copies per phage particle. Using selections on cat oocytes with intact zona pellucida, multiple peptides that specifically recognize and bind to cat ZP were identified. Sequences of the identified peptides are AGSSYTQDS (SEQ ID NO:53); EVNGGSADS (SEQ ID NO:54); EAYPGLDWD (SEQ ID NO:55); and VKSEDPSLN (SEQ ID NO:56).

Example 9

Effect of Specific Landscape Phage on Fertility in Mice

Figure 13:
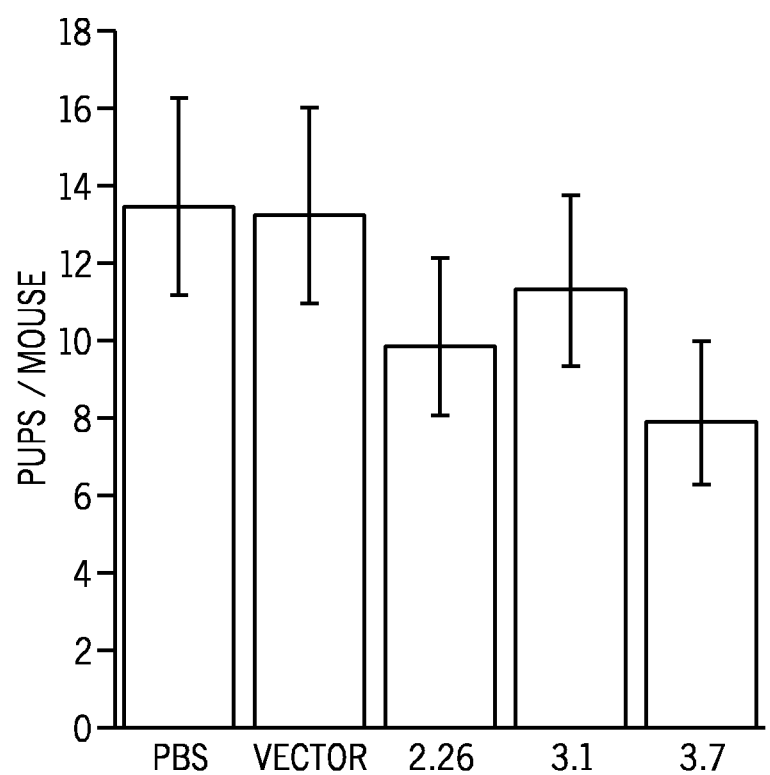
FIG. 13. illustrates the number of pups/mouse treated with landscape phage-based vaccines having heterologous peptide sequences. The height of the bars represent the estimated mean number of pups/mother and the error bars represent the lower and upper 95% confidence limits on those estimates. The data were analyzed using generalized linear model (GLM) procedure in SAS.

Three ZP-binding phage constructs were tested for reduction of pup numbers in preliminary fertility trials in mice (FIG. 12). The whole landscape phage particles carried the following peptides: a) phage clone 3.7—EPGGMVGSD (SEQ ID NO:49); b) phage clone 2.26—EVNGGSADS (SEQ ID NO:54); and c) phage clone 3.1—DDLNSFVND (SEQ ID NO:47). The immunized mice were paired 2 females to 1 male. The total number of mice per group were 8 females and 4 males. The 3.7 group had a significantly lower mean (7.89) number of pups/mouse than PBS controls (13.50) and phage vector controls (13.25), in both cases $p<0.001$ (FIG. 13). The 2.26 group had significantly lower mean (9.89) number of pups as compared to PBS controls (13.50), with a p-value=0.029. A significant reduction in the numbers of pups in a very prolific outbred CD1 mouse strain was observed. No adjuvant was used. Neither dose, the immunization scheme, nor administration route were optimized.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

---

We claim:

1. An isolated polypeptide consisting of the amino acid sequence of SEQ ID NOs: 41, 42, 43, 44, 45, 46, 47, 48, 49, 50, 51, 52, 53, 54, 55, and 56.

2. A recombinant filamentous bacteriophage comprising the polypeptide of claim 1 inserted within a pVIII protein of the bacteriophage.

3. The bacteriophage of claim 2, wherein the filamentous bacteriophage has no more than a single gene 8.

4. An immunogenic composition comprising:
    (a) the polypeptide of claim 1; and
    (b) a suitable excipient, carrier, or diluent.

5. The composition of claim 4, further comprising an adjuvant.

6. An immunogenic composition comprising:
    (a) the bacteriophage of claim 2; and
    (b) a suitable excipient, carrier, or diluent.

7. A method for producing antibodies that bind to sperm, the method comprising administering the immunogenic composition of claim 4 to an animal.

8. A method for producing antibodies that bind to sperm, the method comprising administering the immunogenic composition of claim 6 to an animal.

9. A method for immunizing an animal against conception, the method comprising administering the immunogenic composition of claim 4 to the animal.

10. A method for immunizing an animal against conception, the method comprising administering the immunogenic composition of claim 6 to the animal.

11. An isolated polypeptide having a length of no more than 20 amino acids and comprising an amino acid sequence having 100% identity to the amino acid sequence of SEQ ID NOs: 41, 42, 43, 44, 45, 46, 47, 48, 49, 50, 51, 52, 53, 54, 55, or 56.

12. A recombinant filamentous bacteriophage comprising the polypeptide of claim 11 inserted within a coat protein of the bacteriophage.

* * * * *

SEQUENCE LISTING

```
<160> NUMBER OF SEQ ID NOS: 57

<210> SEQ ID NO 1
<211> LENGTH: 12
<212> TYPE: PRT
<213> ORGANISM: Artificial
<220> FEATURE:
<223> OTHER INFORMATION: Oligopeptide
<220> FEATURE:
<221> NAME/KEY: misc_feature
<222> LOCATION: (1)..(12)

<400> SEQUENCE: 1

Asp Ala Asp Asp Gln Thr His Arg Arg Phe Ser Met
1               5                   10
```

```
<210> SEQ ID NO 2
<211> LENGTH: 12
<212> TYPE: PRT
<213> ORGANISM: Artificial
<220> FEATURE:
<223> OTHER INFORMATION: Oligopeptide
<220> FEATURE:
<221> NAME/KEY: misc_feature
<222> LOCATION: (1)..(12)

<400> SEQUENCE: 2

Asp Ala Asn Arg Leu Pro His Pro Ala Asn Ile Asn
1               5                   10

<210> SEQ ID NO 3
<211> LENGTH: 12
<212> TYPE: PRT
<213> ORGANISM: Artificial
<220> FEATURE:
<223> OTHER INFORMATION: Oligopeptide
<220> FEATURE:
<221> NAME/KEY: misc_feature
<222> LOCATION: (1)..(12)

<400> SEQUENCE: 3

Asp Leu Asn Gly His Lys Thr Leu Pro Val Ser Lys
1               5                   10

<210> SEQ ID NO 4
<211> LENGTH: 12
<212> TYPE: PRT
<213> ORGANISM: Artificial
<220> FEATURE:
<223> OTHER INFORMATION: Oligopeptide
<220> FEATURE:
<221> NAME/KEY: misc_feature
<222> LOCATION: (1)..(12)

<400> SEQUENCE: 4

Asn Ile Gly Leu Pro His Asp Leu His Lys Arg Leu
1               5                   10

<210> SEQ ID NO 5
<211> LENGTH: 12
<212> TYPE: PRT
<213> ORGANISM: Artificial
<220> FEATURE:
<223> OTHER INFORMATION: Oligopeptide
<220> FEATURE:
<221> NAME/KEY: misc_feature
<222> LOCATION: (1)..(12)

<400> SEQUENCE: 5

Gly Leu His Asn Asn Leu His Ala Thr Thr Pro Glu
1               5                   10

<210> SEQ ID NO 6
<211> LENGTH: 12
<212> TYPE: PRT
<213> ORGANISM: Artificial
<220> FEATURE:
<223> OTHER INFORMATION: Oligopeptide
<220> FEATURE:
<221> NAME/KEY: misc_feature
<222> LOCATION: (1)..(12)

<400> SEQUENCE: 6

Gln Ser Ala Ala Trp Tyr Pro Trp Ser Ala Asp His
1               5                   10
```

```
<210> SEQ ID NO 7
<211> LENGTH: 12
<212> TYPE: PRT
<213> ORGANISM: Artificial
<220> FEATURE:
<223> OTHER INFORMATION: Oligopeptide
<220> FEATURE:
<221> NAME/KEY: misc_feature
<222> LOCATION: (1)..(12)

<400> SEQUENCE: 7

Tyr Thr Val Ser Met Pro Asn Val Lys Asp Ala Ala
1               5                   10

<210> SEQ ID NO 8
<211> LENGTH: 12
<212> TYPE: PRT
<213> ORGANISM: Artificial
<220> FEATURE:
<223> OTHER INFORMATION: Oligopeptide
<220> FEATURE:
<221> NAME/KEY: misc_feature
<222> LOCATION: (1)..(12)

<400> SEQUENCE: 8

Tyr Met Pro Asn Pro Phe Thr Ala Ser Lys Trp Lys
1               5                   10

<210> SEQ ID NO 9
<211> LENGTH: 12
<212> TYPE: PRT
<213> ORGANISM: Artificial
<220> FEATURE:
<223> OTHER INFORMATION: Oligopeptide
<220> FEATURE:
<221> NAME/KEY: misc_feature
<222> LOCATION: (1)..(12)

<400> SEQUENCE: 9

Gly Gln Ile Met Pro Leu Pro Thr Asn Leu Leu Val
1               5                   10

<210> SEQ ID NO 10
<211> LENGTH: 12
<212> TYPE: PRT
<213> ORGANISM: Artificial
<220> FEATURE:
<223> OTHER INFORMATION: Oligopeptide
<220> FEATURE:
<221> NAME/KEY: misc_feature
<222> LOCATION: (1)..(12)

<400> SEQUENCE: 10

Ser Thr Thr Leu Pro Met Gly Ser Asn Ala His Leu
1               5                   10

<210> SEQ ID NO 11
<211> LENGTH: 12
<212> TYPE: PRT
<213> ORGANISM: Artificial
<220> FEATURE:
<223> OTHER INFORMATION: Oligopeptide
<220> FEATURE:
<221> NAME/KEY: misc_feature
<222> LOCATION: (1)..(12)

<400> SEQUENCE: 11

Thr Tyr Leu Lys Ala Asp Ser Leu Phe Ser Arg Val
```

<210> SEQ ID NO 12
<211> LENGTH: 12
<212> TYPE: PRT
<213> ORGANISM: Artificial
<220> FEATURE:
<223> OTHER INFORMATION: Oligopeptide
<220> FEATURE:
<221> NAME/KEY: misc_feature
<222> LOCATION: (1)..(12)
<220> FEATURE:
<221> NAME/KEY: Variable
<222> LOCATION: (4)..(4)
<223> OTHER INFORMATION: "Xaa" in position #4 is a naturally occurring amino acid
<220> FEATURE:
<221> NAME/KEY: Variable
<222> LOCATION: (6)..(6)
<223> OTHER INFORMATION: "Xaa" in position #6 is a naturally occurring amino acid
<220> FEATURE:
<221> NAME/KEY: Variable
<222> LOCATION: (8)..(8)
<223> OTHER INFORMATION: "Xaa" in position #8 is a naturally occurring amino acid
<220> FEATURE:
<221> NAME/KEY: Variable
<222> LOCATION: (9)..(9)
<223> OTHER INFORMATION: "Xaa" in position #9 is a naturally occurring amino acid
<220> FEATURE:
<221> NAME/KEY: Variable
<222> LOCATION: (11)..(11)
<223> OTHER INFORMATION: "Xaa" in position #11 is a naturally occurring amino acid
<220> FEATURE:
<221> NAME/KEY: Variable
<222> LOCATION: (12)..(12)
<223> OTHER INFORMATION: "Xaa" in position #12 is a naturally occurring amino acid

<400> SEQUENCE: 12

Thr Thr Leu Xaa Thr Xaa Ser Xaa Xaa His Xaa Xaa
1               5                   10

<210> SEQ ID NO 13
<211> LENGTH: 12
<212> TYPE: PRT
<213> ORGANISM: Artificial
<220> FEATURE:
<223> OTHER INFORMATION: Oligopeptide
<220> FEATURE:
<221> NAME/KEY: misc_feature
<222> LOCATION: (1)..(12)
<220> FEATURE:
<221> NAME/KEY: Variable
<222> LOCATION: (2)..(2)
<223> OTHER INFORMATION: "Xaa" in position #2 is a naturally occurring amino acid
<220> FEATURE:
<221> NAME/KEY: Variable
<222> LOCATION: (4)..(4)
<223> OTHER INFORMATION: "Xaa" in position #4 is a naturally occurring amino acid
<220> FEATURE:
<221> NAME/KEY: Variable
<222> LOCATION: (8)..(8)
<223> OTHER INFORMATION: "Xaa" in position #8 is a naturally occurring amino acid
<220> FEATURE:
<221> NAME/KEY: Variable
<222> LOCATION: (9)..(9)
<223> OTHER INFORMATION: "Xaa" in position #9 is a naturally occurring amino acid
<220> FEATURE:

```
<221> NAME/KEY: Variable
<222> LOCATION: (10)..(10)
<223> OTHER INFORMATION: "Xaa" in position #10 is a naturally occurring
      amino acid
<220> FEATURE:
<221> NAME/KEY: Variable
<222> LOCATION: (11)..(11)
<223> OTHER INFORMATION: "Xaa" in position #11 is a naturally occurring
      amino acid
<220> FEATURE:
<221> NAME/KEY: Variable
<222> LOCATION: (12)..(12)
<223> OTHER INFORMATION: "Xaa" in position #12 is a naturally occurring
      amino acid

<400> SEQUENCE: 13

Asp Xaa Asn Xaa Leu Pro His Xaa Xaa Xaa Xaa Xaa
1               5                   10

<210> SEQ ID NO 14
<211> LENGTH: 12
<212> TYPE: PRT
<213> ORGANISM: Artificial
<220> FEATURE:
<223> OTHER INFORMATION: Oligopeptide
<220> FEATURE:
<221> NAME/KEY: misc_feature
<222> LOCATION: (1)..(12)
<220> FEATURE:
<221> NAME/KEY: Variable
<222> LOCATION: (1)..(1)
<223> OTHER INFORMATION: "Xaa" in position #1 is a naturally occurring
      amino acid
<220> FEATURE:
<221> NAME/KEY: Variable
<222> LOCATION: (4)..(4)
<223> OTHER INFORMATION: "Xaa" in position #4 is a naturally occurring
      amino acid
<220> FEATURE:
<221> NAME/KEY: Variable
<222> LOCATION: (5)..(5)
<223> OTHER INFORMATION: "Xaa" in position #5 is a naturally occurring
      amino acid
<220> FEATURE:
<221> NAME/KEY: Variable
<222> LOCATION: (6)..(6)
<223> OTHER INFORMATION: "Xaa" in position #6 is a naturally occurring
      amino acid
<220> FEATURE:
<221> NAME/KEY: Variable
<222> LOCATION: (9)..(9)
<223> OTHER INFORMATION: "Xaa" in position #9 is a naturally occurring
      amino acid
<220> FEATURE:
<221> NAME/KEY: Variable
<222> LOCATION: (11)..(11)
<223> OTHER INFORMATION: "Xaa" in position #11 is a naturally occurring
      amino acid

<400> SEQUENCE: 14

Xaa Gly Leu Xaa Xaa Xaa Leu His Xaa Thr Xaa Pro
1               5                   10

<210> SEQ ID NO 15
<211> LENGTH: 11
<212> TYPE: PRT
<213> ORGANISM: Artificial
<220> FEATURE:
<223> OTHER INFORMATION: Oligopeptide
<220> FEATURE:
<221> NAME/KEY: misc_feature
<222> LOCATION: (1)..(11)
<220> FEATURE:
<221> NAME/KEY: variable
<222> LOCATION: (1)..(1)
```

```
<223> OTHER INFORMATION: "Xaa" in position #1 is a naturally occurring
      amino acid
<220> FEATURE:
<221> NAME/KEY: variable
<222> LOCATION: (2)..(2)
<223> OTHER INFORMATION: "Xaa" in position #2 is a naturally occurring
      amino acid
<220> FEATURE:
<221> NAME/KEY: variable
<222> LOCATION: (8)..(8)
<223> OTHER INFORMATION: "Xaa" in position #8 is a naturally occurring
      amino acid
<220> FEATURE:
<221> NAME/KEY: variable
<222> LOCATION: (9)..(9)
<223> OTHER INFORMATION: "Xaa" in position #9 is a naturally occurring
      amino acid
<220> FEATURE:
<221> NAME/KEY: variable
<222> LOCATION: (10)..(10)
<223> OTHER INFORMATION: "Xaa" in position #10 is a naturally occurring
      amino acid

<400> SEQUENCE: 15

Xaa Xaa Met Pro Asn Pro Val Xaa Xaa Ala Xaa
1               5                   10

<210> SEQ ID NO 16
<211> LENGTH: 11
<212> TYPE: PRT
<213> ORGANISM: Artificial
<220> FEATURE:
<223> OTHER INFORMATION: oligopeptide
<220> FEATURE:
<221> NAME/KEY: misc_feature
<222> LOCATION: (1)..(11)
<220> FEATURE:
<221> NAME/KEY: Variable
<222> LOCATION: (1)..(1)
<223> OTHER INFORMATION: "Xaa" in position #1 is a naturally occurring
      amino acid
<220> FEATURE:
<221> NAME/KEY: Variable
<222> LOCATION: (4)..(4)
<223> OTHER INFORMATION: "Xaa" in position #4 is a naturally occurring
      amino acid
<220> FEATURE:
<221> NAME/KEY: Variable
<222> LOCATION: (5)..(5)
<223> OTHER INFORMATION: "Xaa" in position #5 is a naturally occurring
      amino acid
<220> FEATURE:
<221> NAME/KEY: Variable
<222> LOCATION: (9)..(9)
<223> OTHER INFORMATION: "Xaa" in position #9 is a naturally occurring
      amino acid
<220> FEATURE:
<221> NAME/KEY: Variable
<222> LOCATION: (11)..(11)
<223> OTHER INFORMATION: "Xaa" in position #11 is a naturally occurring
      amino acid

<400> SEQUENCE: 16

Xaa Gly Ser Xaa Xaa Thr Leu Pro Xaa Ser Xaa
1               5                   10

<210> SEQ ID NO 17
<211> LENGTH: 12
<212> TYPE: PRT
<213> ORGANISM: Artificial
<220> FEATURE:
<223> OTHER INFORMATION: oligopeptide
<220> FEATURE:
<221> NAME/KEY: misc_feature
<222> LOCATION: (1)..(12)
```

```
<220> FEATURE:
<221> NAME/KEY: Variable
<222> LOCATION: (2)..(2)
<223> OTHER INFORMATION: "Xaa" in position #2 is a naturally occurring
      amino acid
<220> FEATURE:
<221> NAME/KEY: Variable
<222> LOCATION: (4)..(4)
<223> OTHER INFORMATION: "Xaa" in position #4 is a naturally occurring
      amino acid
<220> FEATURE:
<221> NAME/KEY: Variable
<222> LOCATION: (5)..(5)
<223> OTHER INFORMATION: "Xaa" in position #5 is a naturally occurring
      amino acid
<220> FEATURE:
<221> NAME/KEY: Variable
<222> LOCATION: (6)..(6)
<223> OTHER INFORMATION: "Xaa" in position #6 is a naturally occurring
      amino acid
<220> FEATURE:
<221> NAME/KEY: Variable
<222> LOCATION: (9)..(9)
<223> OTHER INFORMATION: "Xaa" in position #9 is a naturally occurring
      amino acid
<220> FEATURE:
<221> NAME/KEY: Variable
<222> LOCATION: (10)..(10)
<223> OTHER INFORMATION: "Xaa" in position #10 is a naturally occurring
      amino acid
<220> FEATURE:
<221> NAME/KEY: Variable
<222> LOCATION: (11)..(11)
<223> OTHER INFORMATION: "Xaa" in position #11 is a naturally occurring
      amino acid
<220> FEATURE:
<221> NAME/KEY: Variable
<222> LOCATION: (12)..(12)
<223> OTHER INFORMATION: "Xaa" in position #12 is a naturally occurring
      amino acid

<400> SEQUENCE: 17

Gln Xaa Ala Xaa Xaa Xaa Pro Trp Xaa Xaa Xaa Xaa
1               5                   10

<210> SEQ ID NO 18
<211> LENGTH: 12
<212> TYPE: PRT
<213> ORGANISM: Artificial
<220> FEATURE:
<223> OTHER INFORMATION: oligopeptide
<220> FEATURE:
<221> NAME/KEY: misc_feature
<222> LOCATION: (1)..(12)

<400> SEQUENCE: 18

Thr Leu Gly Trp Thr Ala Asn Glu Ala Pro Arg Arg
1               5                   10

<210> SEQ ID NO 19
<211> LENGTH: 12
<212> TYPE: PRT
<213> ORGANISM: Artificial
<220> FEATURE:
<223> OTHER INFORMATION: oligopeptide
<220> FEATURE:
<221> NAME/KEY: misc_feature
<222> LOCATION: (1)..(12)

<400> SEQUENCE: 19

Leu Leu Ala Asp Thr Thr His His Arg Pro Trp Thr
1               5                   10
```

```
<210> SEQ ID NO 20
<211> LENGTH: 12
<212> TYPE: PRT
<213> ORGANISM: Artificial
<220> FEATURE:
<223> OTHER INFORMATION: oligopeptide
<220> FEATURE:
<221> NAME/KEY: misc_feature
<222> LOCATION: (1)..(12)

<400> SEQUENCE: 20

Ser Gln Ser Pro Ala Met Tyr Ser Pro Thr Arg Pro
1               5                   10

<210> SEQ ID NO 21
<211> LENGTH: 12
<212> TYPE: PRT
<213> ORGANISM: Artificial
<220> FEATURE:
<223> OTHER INFORMATION: oligopeptide
<220> FEATURE:
<221> NAME/KEY: misc_feature
<222> LOCATION: (1)..(12)

<400> SEQUENCE: 21

Ala Val Thr Gln His Leu Lys Phe Lys Gly Phe Asn
1               5                   10

<210> SEQ ID NO 22
<211> LENGTH: 12
<212> TYPE: PRT
<213> ORGANISM: Artificial
<220> FEATURE:
<223> OTHER INFORMATION: oligopeptide
<220> FEATURE:
<221> NAME/KEY: misc_feature
<222> LOCATION: (1)..(12)

<400> SEQUENCE: 22

Ala Asn Phe Asn Met Thr His His Gln Gly His Lys
1               5                   10

<210> SEQ ID NO 23
<211> LENGTH: 12
<212> TYPE: PRT
<213> ORGANISM: Artificial
<220> FEATURE:
<223> OTHER INFORMATION: oligopeptide
<220> FEATURE:
<221> NAME/KEY: misc_feature
<222> LOCATION: (1)..(12)
<220> FEATURE:
<221> NAME/KEY: Variable
<222> LOCATION: (1)..(1)
<223> OTHER INFORMATION: "Xaa" in position #1 is a naturally occurring
      amino acid
<220> FEATURE:
<221> NAME/KEY: Variable
<222> LOCATION: (2)..(2)
<223> OTHER INFORMATION: "Xaa" in position #2 is a naturally occurring
      amino acid
<220> FEATURE:
<221> NAME/KEY: Variable
<222> LOCATION: (7)..(7)
<223> OTHER INFORMATION: "Xaa" in position #7 is a naturally occurring
      amino acid
<220> FEATURE:
<221> NAME/KEY: Variable
<222> LOCATION: (8)..(8)
<223> OTHER INFORMATION: "Xaa" in position #8 is a naturally occurring
      amino acid
<220> FEATURE:
<221> NAME/KEY: Variable
```

```
<222> LOCATION: (9)..(9)
<223> OTHER INFORMATION: "Xaa" in position #9 is a naturally occurring
      amino acid
<220> FEATURE:
<221> NAME/KEY: Variable
<222> LOCATION: (10)..(10)
<223> OTHER INFORMATION: "Xaa" in position #10 is a naturally occurring
      amino acid
<220> FEATURE:
<221> NAME/KEY: Variable
<222> LOCATION: (11)..(11)
<223> OTHER INFORMATION: "Xaa" in position #11 is a naturally occurring
      amino acid
<220> FEATURE:
<221> NAME/KEY: Variable
<222> LOCATION: (12)..(12)
<223> OTHER INFORMATION: "Xaa" in position #12 is a naturally occurring
      amino acid

<400> SEQUENCE: 23

Xaa Xaa Thr Thr His His Xaa Xaa Xaa Xaa Xaa Xaa
1               5                   10

<210> SEQ ID NO 24
<211> LENGTH: 12
<212> TYPE: PRT
<213> ORGANISM: Artificial
<220> FEATURE:
<223> OTHER INFORMATION: oligopeptide
<220> FEATURE:
<221> NAME/KEY: misc_feature
<222> LOCATION: (1)..(12)
<220> FEATURE:
<221> NAME/KEY: Variable
<222> LOCATION: (1)..(1)
<223> OTHER INFORMATION: "Xaa" in position #1 is a naturally occurring
      amino acid
<220> FEATURE:
<221> NAME/KEY: Variable
<222> LOCATION: (2)..(2)
<223> OTHER INFORMATION: "Xaa" in position #2 is a naturally occurring
      amino acid
<220> FEATURE:
<221> NAME/KEY: Variable
<222> LOCATION: (4)..(4)
<223> OTHER INFORMATION: "Xaa" in position #4 is a naturally occurring
      amino acid
<220> FEATURE:
<221> NAME/KEY: Variable
<222> LOCATION: (5)..(5)
<223> OTHER INFORMATION: "Xaa" in position #5 is a naturally occurring
      amino acid
<220> FEATURE:
<221> NAME/KEY: Variable
<222> LOCATION: (7)..(7)
<223> OTHER INFORMATION: "Xaa" in position #7 is a naturally occurring
      amino acid
<220> FEATURE:
<221> NAME/KEY: Variable
<222> LOCATION: (8)..(8)
<223> OTHER INFORMATION: "Xaa" in position #8 is a naturally occurring
      amino acid
<220> FEATURE:
<221> NAME/KEY: Variable
<222> LOCATION: (11)..(11)
<223> OTHER INFORMATION: "Xaa" in position #11 is a naturally occurring
      amino acid
<220> FEATURE:
<221> NAME/KEY: Variable
<222> LOCATION: (12)..(12)
<223> OTHER INFORMATION: "Xaa" in position #12 is a naturally occurring
      amino acid

<400> SEQUENCE: 24

Xaa Xaa Asn Xaa Xaa Leu Xaa Xaa Pro Ala Xaa Xaa
1               5                   10
```

```
<210> SEQ ID NO 25
<211> LENGTH: 12
<212> TYPE: PRT
<213> ORGANISM: Artificial
<220> FEATURE:
<223> OTHER INFORMATION: oligopeptide
<220> FEATURE:
<221> NAME/KEY: misc_feature
<222> LOCATION: (1)..(12)
<220> FEATURE:
<221> NAME/KEY: Variable
<222> LOCATION: (1)..(1)
<223> OTHER INFORMATION: "Xaa" in position #1 is a naturally occurring
      amino acid
<220> FEATURE:
<221> NAME/KEY: Variable
<222> LOCATION: (2)..(2)
<223> OTHER INFORMATION: "Xaa" in position #2 is a naturally occurring
      amino acid
<220> FEATURE:
<221> NAME/KEY: Variable
<222> LOCATION: (4)..(4)
<223> OTHER INFORMATION: "Xaa" in position #4 is a naturally occurring
      amino acid
<220> FEATURE:
<221> NAME/KEY: Variable
<222> LOCATION: (5)..(5)
<223> OTHER INFORMATION: "Xaa" in position #5 is a naturally occurring
      amino acid
<220> FEATURE:
<221> NAME/KEY: Variable
<222> LOCATION: (6)..(6)
<223> OTHER INFORMATION: "Xaa" in position #6 is a naturally occurring
      amino acid
<220> FEATURE:
<221> NAME/KEY: Variable
<222> LOCATION: (7)..(7)
<223> OTHER INFORMATION: "Xaa" in position #7 is a naturally occurring
      amino acid
<220> FEATURE:
<221> NAME/KEY: Variable
<222> LOCATION: (8)..(8)
<223> OTHER INFORMATION: "Xaa" in position #8 is a naturally occurring
      amino acid
<220> FEATURE:
<221> NAME/KEY: Variable
<222> LOCATION: (11)..(11)
<223> OTHER INFORMATION: "Xaa" in position #11 is a naturally occurring
      amino acid
<220> FEATURE:
<221> NAME/KEY: Variable
<222> LOCATION: (12)..(12)
<223> OTHER INFORMATION: "Xaa" in position #12 is a naturally occurring
      amino acid

<400> SEQUENCE: 25

Xaa Xaa Ala Xaa Xaa Xaa Xaa Xaa Arg Pro Xaa Xaa
1               5                   10

<210> SEQ ID NO 26
<211> LENGTH: 12
<212> TYPE: PRT
<213> ORGANISM: Artificial
<220> FEATURE:
<223> OTHER INFORMATION: oligopeptide
<220> FEATURE:
<221> NAME/KEY: misc_feature
<222> LOCATION: (1)..(12)
<220> FEATURE:
<221> NAME/KEY: Variable
<222> LOCATION: (1)..(1)
<223> OTHER INFORMATION: "Xaa" in position #1 is a naturally occurring
      amino acid
<220> FEATURE:
<221> NAME/KEY: Variable
```

```
<222> LOCATION: (2)..(2)
<223> OTHER INFORMATION: "Xaa" in position #2 is a naturally occurring
      amino acid
<220> FEATURE:
<221> NAME/KEY: Variable
<222> LOCATION: (5)..(5)
<223> OTHER INFORMATION: "Xaa" in position #5 is a naturally occurring
      amino acid
<220> FEATURE:
<221> NAME/KEY: Variable
<222> LOCATION: (6)..(6)
<223> OTHER INFORMATION: "Xaa" in position #6 is a naturally occurring
      amino acid
<220> FEATURE:
<221> NAME/KEY: Variable
<222> LOCATION: (10)..(10)
<223> OTHER INFORMATION: "Xaa" in position #10 is a naturally occurring
      amino acid
<220> FEATURE:
<221> NAME/KEY: Variable
<222> LOCATION: (11)..(11)
<223> OTHER INFORMATION: "Xaa" in position #11 is a naturally occurring
      amino acid
<220> FEATURE:
<221> NAME/KEY: Variable
<222> LOCATION: (12)..(12)
<223> OTHER INFORMATION: "Xaa" in position #12 is a naturally occurring
      amino acid

<400> SEQUENCE: 26

Xaa Xaa Ser Ser Xaa Xaa Ser Ala Ser Xaa Xaa Xaa
1               5                   10

<210> SEQ ID NO 27
<211> LENGTH: 7
<212> TYPE: PRT
<213> ORGANISM: Artificial
<220> FEATURE:
<223> OTHER INFORMATION: Phage library random peptide insert

<400> SEQUENCE: 27

Leu Asn Ser Phe Leu Arg Ser
1               5

<210> SEQ ID NO 28
<211> LENGTH: 7
<212> TYPE: PRT
<213> ORGANISM: Artificial
<220> FEATURE:
<223> OTHER INFORMATION: Phage library random peptide insert

<400> SEQUENCE: 28

Leu Ser Thr Ala Leu Arg Ser
1               5

<210> SEQ ID NO 29
<211> LENGTH: 7
<212> TYPE: PRT
<213> ORGANISM: Artificial
<220> FEATURE:
<223> OTHER INFORMATION: Phage library random peptide inser

<400> SEQUENCE: 29

Ser Ser Trp Tyr Arg Gly Ala
1               5

<210> SEQ ID NO 30
<211> LENGTH: 7
<212> TYPE: PRT
<213> ORGANISM: Artificial
<220> FEATURE:
```

<223> OTHER INFORMATION: Phage library random peptide insert

<400> SEQUENCE: 30

Thr Gly Thr Ser Thr Arg Ala
1               5

<210> SEQ ID NO 31
<211> LENGTH: 12
<212> TYPE: PRT
<213> ORGANISM: Artificial
<220> FEATURE:
<223> OTHER INFORMATION: Phage library random peptide insert

<400> SEQUENCE: 31

Tyr Leu Pro Ile Tyr Thr Ile Pro Ser Met Val Tyr
1               5                   10

<210> SEQ ID NO 32
<211> LENGTH: 12
<212> TYPE: PRT
<213> ORGANISM: Artificial
<220> FEATURE:
<223> OTHER INFORMATION: Phage library random peptide insert

<400> SEQUENCE: 32

Asn Asn Gln Ser Pro Ile Leu Lys Leu Ser Ile His
1               5                   10

<210> SEQ ID NO 33
<211> LENGTH: 12
<212> TYPE: PRT
<213> ORGANISM: Artificial
<220> FEATURE:
<223> OTHER INFORMATION: Phage library random peptide insert

<400> SEQUENCE: 33

Ala His Pro Asn Thr Ala Pro Ile His Pro Lys Phe
1               5                   10

<210> SEQ ID NO 34
<211> LENGTH: 9
<212> TYPE: PRT
<213> ORGANISM: Artificial
<220> FEATURE:
<223> OTHER INFORMATION: Phage library random peptide insert

<400> SEQUENCE: 34

Cys Leu Asn Ser Phe Leu Arg Ser Cys
1               5

<210> SEQ ID NO 35
<211> LENGTH: 12
<212> TYPE: PRT
<213> ORGANISM: Artificial
<220> FEATURE:
<223> OTHER INFORMATION: Phage library random peptide insert

<400> SEQUENCE: 35

Cys Leu Asn Ser Phe Leu Arg Ser Cys Lys Gly Gly
1               5                   10

<210> SEQ ID NO 36
<211> LENGTH: 9
<212> TYPE: PRT
<213> ORGANISM: Artificial
<220> FEATURE:
<223> OTHER INFORMATION: Phage library random peptide insert

```
<400> SEQUENCE: 36

Cys Ser Ser Trp Tyr Arg Gly Ala Cys
1               5

<210> SEQ ID NO 37
<211> LENGTH: 13
<212> TYPE: PRT
<213> ORGANISM: Artificial
<220> FEATURE:
<223> OTHER INFORMATION: Phage library random peptide insert

<400> SEQUENCE: 37

Cys Ser Ser Trp Tyr Arg Gly Ala Cys Lys Gly Gly Tyr
1               5                   10

<210> SEQ ID NO 38
<211> LENGTH: 14
<212> TYPE: PRT
<213> ORGANISM: Artificial
<220> FEATURE:
<223> OTHER INFORMATION: Phage library random peptide insert

<400> SEQUENCE: 38

Tyr Leu Pro Ile Tyr Thr Ile Pro Ser Met Val Tyr Gly Gly
1               5                   10

<210> SEQ ID NO 39
<211> LENGTH: 14
<212> TYPE: PRT
<213> ORGANISM: Artificial
<220> FEATURE:
<223> OTHER INFORMATION: Phage library random peptide insert

<400> SEQUENCE: 39

Asn Asn Gln Ser Pro Ile Leu Lys Leu Ser Ile His Gly Gly
1               5                   10

<210> SEQ ID NO 40
<211> LENGTH: 12
<212> TYPE: PRT
<213> ORGANISM: Artificial
<220> FEATURE:
<223> OTHER INFORMATION: Phage library random peptide insert

<400> SEQUENCE: 40

Tyr Leu Pro Val Gly Gly Leu Arg Arg Ile Gly Gly
1               5                   10

<210> SEQ ID NO 41
<211> LENGTH: 9
<212> TYPE: PRT
<213> ORGANISM: Artificial
<220> FEATURE:
<223> OTHER INFORMATION: Phage library random peptide insert

<400> SEQUENCE: 41

Asp Pro Gly Leu Ser Leu Gly Asp Asp
1               5

<210> SEQ ID NO 42
<211> LENGTH: 9
<212> TYPE: PRT
<213> ORGANISM: Artificial
<220> FEATURE:
<223> OTHER INFORMATION: Phage library random peptide insert
```

```
<400> SEQUENCE: 42

Ala Tyr Asn Leu Gly Glu Gly Asp Thr
1               5

<210> SEQ ID NO 43
<211> LENGTH: 9
<212> TYPE: PRT
<213> ORGANISM: Artificial
<220> FEATURE:
<223> OTHER INFORMATION: Phage library random peptide insert

<400> SEQUENCE: 43

Gly Gln Gln Gly Leu Asn Gly Asp Ser
1               5

<210> SEQ ID NO 44
<211> LENGTH: 9
<212> TYPE: PRT
<213> ORGANISM: Artificial
<220> FEATURE:
<223> OTHER INFORMATION: Phage library random peptide insert

<400> SEQUENCE: 44

Asp Val Gly Gly Gly Thr Gly Thr Glu
1               5

<210> SEQ ID NO 45
<211> LENGTH: 9
<212> TYPE: PRT
<213> ORGANISM: Artificial
<220> FEATURE:
<223> OTHER INFORMATION: Phage library random peptide insert

<400> SEQUENCE: 45

Gly Pro Asn Ser Ser Asp Ala Asp Ser
1               5

<210> SEQ ID NO 46
<211> LENGTH: 9
<212> TYPE: PRT
<213> ORGANISM: Artificial
<220> FEATURE:
<223> OTHER INFORMATION: Phage library random peptide insert

<400> SEQUENCE: 46

Gly Glu Gly Gly Tyr Gly Ser His Asp
1               5

<210> SEQ ID NO 47
<211> LENGTH: 9
<212> TYPE: PRT
<213> ORGANISM: Artificial
<220> FEATURE:
<223> OTHER INFORMATION: Phage library random peptide insert

<400> SEQUENCE: 47

Asp Asp Leu Asn Ser Phe Val Asn Asp
1               5

<210> SEQ ID NO 48
<211> LENGTH: 9
<212> TYPE: PRT
<213> ORGANISM: Artificial
<220> FEATURE:
<223> OTHER INFORMATION: Phage library random peptide insert

<400> SEQUENCE: 48
```

```
Ala Asp Leu Ala Ala Phe Tyr Asp Asp
1               5

<210> SEQ ID NO 49
<211> LENGTH: 9
<212> TYPE: PRT
<213> ORGANISM: Artificial
<220> FEATURE:
<223> OTHER INFORMATION: Phage library random peptide insert

<400> SEQUENCE: 49

Glu Pro Gly Gly Met Val Gly Ser Asp
1               5

<210> SEQ ID NO 50
<211> LENGTH: 9
<212> TYPE: PRT
<213> ORGANISM: Artificial
<220> FEATURE:
<223> OTHER INFORMATION: Phage library random peptide insert

<400> SEQUENCE: 50

Asp Gly Val Tyr Leu Val Gly Asp Asp
1               5

<210> SEQ ID NO 51
<211> LENGTH: 9
<212> TYPE: PRT
<213> ORGANISM: Artificial
<220> FEATURE:
<223> OTHER INFORMATION: Phage library random peptide insert

<400> SEQUENCE: 51

Asp Trp Ser Gly Gln Asp Val Glu Asn
1               5

<210> SEQ ID NO 52
<211> LENGTH: 9
<212> TYPE: PRT
<213> ORGANISM: Artificial
<220> FEATURE:
<223> OTHER INFORMATION: Phage library random peptide insert

<400> SEQUENCE: 52

Gly Met Val Gly Ser Gly Tyr Asp Ser
1               5

<210> SEQ ID NO 53
<211> LENGTH: 9
<212> TYPE: PRT
<213> ORGANISM: Artificial
<220> FEATURE:
<223> OTHER INFORMATION: Phage library random peptide insert

<400> SEQUENCE: 53

Ala Gly Ser Ser Tyr Thr Gln Asp Ser
1               5

<210> SEQ ID NO 54
<211> LENGTH: 9
<212> TYPE: PRT
<213> ORGANISM: Artificial
<220> FEATURE:
<223> OTHER INFORMATION: Phage library random peptide insert

<400> SEQUENCE: 54
```

```
Glu Val Asn Gly Gly Ser Ala Asp Ser
1               5

<210> SEQ ID NO 55
<211> LENGTH: 9
<212> TYPE: PRT
<213> ORGANISM: Artificial
<220> FEATURE:
<223> OTHER INFORMATION: Phage library random peptide insert

<400> SEQUENCE: 55

Glu Ala Tyr Pro Gly Leu Asp Trp Asp
1               5

<210> SEQ ID NO 56
<211> LENGTH: 9
<212> TYPE: PRT
<213> ORGANISM: Artificial
<220> FEATURE:
<223> OTHER INFORMATION: Phage library random peptide insert

<400> SEQUENCE: 56

Val Lys Ser Glu Asp Pro Ser Leu Asn
1               5

<210> SEQ ID NO 57
<211> LENGTH: 12
<212> TYPE: PRT
<213> ORGANISM: Artificial
<220> FEATURE:
<223> OTHER INFORMATION: Phage library random insert

<400> SEQUENCE: 57

Tyr Leu Pro Val Gly Gly Leu Arg Arg Ile Gly Gly
1               5                   10
```